United States Patent
Jacobsen et al.

(10) Patent No.: US 8,932,235 B2
(45) Date of Patent: *Jan. 13, 2015

(54) MEDICAL DEVICE FOR NAVIGATION THROUGH ANATOMY AND METHOD OF MAKING SAME

(75) Inventors: Stephen C. Jacobsen, Salt Lake City, UT (US); Clark C. Davis, Holladay, UT (US); Clay W. Northrop, Salt Lake City, UT (US); Ted W. Layman, Park City, UT (US); Kevin T. Olson, Salt Lake City, UT (US); Edward J. Snyder, Park City, UT (US); D. Kent Backman, Salt Lake City, UT (US); Todd H. Turnlund, Park City, UT (US)

(73) Assignee: Precision Vascular Systems, Inc., West Valley City, UT (US)

(*) Notice: Subject to any disclaimer, the term of this patent is extended or adjusted under 35 U.S.C. 154(b) by 1735 days.

This patent is subject to a terminal disclaimer.

(21) Appl. No.: 11/831,931

(22) Filed: Jul. 31, 2007

(65) Prior Publication Data

US 2008/0021407 A1 Jan. 24, 2008

Related U.S. Application Data

(63) Continuation of application No. 10/604,504, filed on Jul. 25, 2003, now Pat. No. 7,878,984.

(60) Provisional application No. 60/399,046, filed on Jul. 25, 2002.

(51) Int. Cl.
*A61M 25/00* (2006.01)
*A61M 25/09* (2006.01)
*A61M 25/01* (2006.01)

(52) U.S. Cl.
CPC .......... *A61M 25/09* (2013.01); *A61M 25/09016* (2013.01); *A61M 25/0013* (2013.01); *A61M 25/01* (2013.01)
USPC ...................................................... 600/585

(58) Field of Classification Search
CPC .......... A61M 25/09; A61M 25/09016; A61M 25/0013; A61M 25/01
USPC ........ 600/585, 434, 435; 128/772; 606/7, 15, 606/159, 200, 80; 607/117–130; 242/387; 336/223; 604/103.09, 103.1, 523, 530, 604/96.01; 623/1.28, 1.14, 1.35, 1.36, 1.2, 623/1.15

See application file for complete search history.

(56) References Cited

U.S. PATENT DOCUMENTS

| | | | |
|---|---|---|---|
| 1,553,227 | A | 9/1925 | Feyk et al. |
| 1,866,888 | A | 7/1932 | Hawley |
| 2,275,827 | A | 3/1942 | Plensler |
| 2,413,805 | A | 1/1947 | Vickers |
| 2,441,166 | A | 5/1948 | Raspert |
| 2,561,890 | A | 7/1951 | Stoddard |

(Continued)

FOREIGN PATENT DOCUMENTS

| | | |
|---|---|---|
| AU | 723040 | 12/1997 |
| AU | 733966 | 4/1998 |

(Continued)

*Primary Examiner* — Brian Szmal
(74) *Attorney, Agent, or Firm* — Seager, Tufte & Wickhem, LLC

(57) ABSTRACT

Medical devices for navigation through anatomy, including guidewires, which may have a core wire, a slotted tubular member, or both. Embodiments may have coils, including non-circular cross-section edge-wound marker coils, extended coil tips, and soldered or glued mesial joint coils. Core wires may have a step, ridge, or taper at the joints to the tubular member, and may be flattened at the distal tip. Radiopaque material may be located inside the tubular member, and the distal tip may be heat treated to make it shapeable. Additional tubular members or coils may be used concentrically or in line and may enhance flexibility, provide radiopacity, reduce friction, or reduce material or manufacturing cost. Tubular members may be chamfered or tapered continuously or incrementally. Slots may be arranged in groups, such as groups of three, and may be equal in depth or unequal in depth to provide a steerable or compressible tip.

15 Claims, 10 Drawing Sheets

(56) References Cited

U.S. PATENT DOCUMENTS

| | | |
|---|---|---|
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Wilson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gurs |
| 4,665,906 A | 5/1987 | Jervis |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gamble |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,358,493 A | 10/1994 | Schweich et al. |
| 5,365,942 A | 11/1994 | Shank |
| 5,365,943 A | 11/1994 | Jansen |
| 5,368,564 A | 11/1994 | Savage |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams et al. |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,460,960 A | 10/1995 | Kim et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |

(56) References Cited

U.S. PATENT DOCUMENTS

| | | | |
|---|---|---|---|
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,622,184 A | 4/1997 | Ashby et al. |
| 5,630,806 A | 5/1997 | Inagaki et al. |
| 5,637,089 A | 6/1997 | Abrams et al. |
| 5,656,011 A | 8/1997 | Uihlein et al. |
| 5,658,264 A | 8/1997 | Samson |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,676,697 A | 10/1997 | McDonald |
| 5,682,894 A | 11/1997 | Orr et al. |
| 5,690,120 A | 11/1997 | Jacobsen et al. |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio, III et al. |
| 5,746,701 A | 5/1998 | Noone |
| 5,769,830 A | 6/1998 | Parker |
| 5,772,609 A | 6/1998 | Nguyen et al. |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,833,632 A | 11/1998 | Jacobsen et al. |
| 5,836,926 A | 11/1998 | Peterson et al. |
| 5,843,050 A | 12/1998 | Jones et al. |
| 5,843,244 A | 12/1998 | Pelton et al. |
| 5,851,203 A | 12/1998 | van Muiden |
| 5,895,378 A | 4/1999 | Nita |
| 5,897,537 A | 4/1999 | Berg et al. |
| 5,902,254 A | 5/1999 | Magram |
| 5,902,290 A | 5/1999 | Peacock, III et al. |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone et al. |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,971,975 A | 10/1999 | Mills et al. |
| 6,001,068 A | 12/1999 | Uchino et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A | 3/2000 | Solar et al. |
| 6,045,547 A | 4/2000 | Ren et al. |
| 6,048,339 A | 4/2000 | Zirps et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,106,485 A | 8/2000 | McMahon |
| 6,106,488 A | 8/2000 | Fleming et al. |
| 6,139,510 A | 10/2000 | Palermo |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| 6,214,042 B1 | 4/2001 | Jacobsen et al. |
| 6,228,073 B1 | 5/2001 | Noone et al. |
| 6,248,082 B1 | 6/2001 | Jafari |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,287,335 B1 * | 9/2001 | Drasler et al. ............... 623/1.28 |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,447,518 B1 * | 9/2002 | Krause et al. ................... 606/80 |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,503,244 B2 | 1/2003 | Hayman |
| 6,508,803 B1 | 1/2003 | Horikawa et al. |
| 6,524,301 B1 | 2/2003 | Wilson et al. |
| 6,530,934 B1 | 3/2003 | Jacobsen et al. |
| 6,547,779 B2 | 4/2003 | Levine et al. |
| 6,553,880 B2 | 4/2003 | Jacobsen et al. |
| 6,556,873 B1 | 4/2003 | Smits |
| 6,579,246 B2 | 6/2003 | Jacobsen et al. |
| 6,602,280 B2 | 8/2003 | Chobotov |
| 6,610,046 B1 | 8/2003 | Usami et al. |
| 6,623,448 B2 | 9/2003 | Slater |
| 6,636,758 B2 | 10/2003 | Sanchez et al. |
| 6,638,266 B2 | 10/2003 | Wilson et al. |
| 6,652,508 B2 | 11/2003 | Griffin et al. |
| 6,663,664 B1 * | 12/2003 | Pacetti ............................ 623/1.2 |
| 6,682,493 B2 | 1/2004 | Mirigian |
| 6,712,826 B2 | 3/2004 | Lui |
| 6,730,095 B2 | 5/2004 | Olson, Jr. et al. |
| 6,749,560 B1 | 6/2004 | Konstorum et al. |
| 6,766,720 B1 | 7/2004 | Jacobsen et al. |
| 6,777,644 B2 | 8/2004 | Peacock, III et al. |
| 6,811,544 B2 | 11/2004 | Schaer |
| 6,837,898 B2 | 1/2005 | Boyle et al. |
| 6,866,642 B2 | 3/2005 | Kellerman et al. |
| 6,887,235 B2 | 5/2005 | O'Connor et al. |
| 6,918,882 B2 | 7/2005 | Skujins et al. |
| 6,997,937 B2 | 2/2006 | Jacobsen et al. |
| 7,001,369 B2 | 2/2006 | Griffin et al. |
| 7,074,197 B2 | 7/2006 | Reynolds et al. |
| 8,257,279 B2 * | 9/2012 | Davis et al. .................. 600/585 |
| 2002/0013540 A1 * | 1/2002 | Jacobsen et al. ............. 600/585 |
| 2002/0019599 A1 | 2/2002 | Rooney et al. |
| 2003/0009208 A1 | 1/2003 | Snyder et al. |
| 2003/0060732 A1 | 3/2003 | Jacobsen et al. |
| 2003/0069522 A1 | 4/2003 | Jacobsen et al. |

(56) References Cited

U.S. PATENT DOCUMENTS

| | | |
|---|---|---|
| 2004/0167437 A1 | 8/2004 | Sharrow et al. |
| 2004/0181174 A2 | 9/2004 | Davis et al. |
| 2004/0181176 A1 | 9/2004 | Jafari et al. |
| 2006/0189896 A1 | 8/2006 | Davis et al. |
| 2006/0264904 A1 | 11/2006 | Kerby et al. |
| 2008/0021347 A1 | 1/2008 | Jacobsen et al. |
| 2008/0021348 A1 | 1/2008 | Jacobsen et al. |
| 2008/0021400 A1 | 1/2008 | Jacobsen et al. |
| 2008/0021401 A1 | 1/2008 | Jacobsen et al. |
| 2008/0021402 A1 | 1/2008 | Jacobsen et al. |
| 2008/0021403 A1 | 1/2008 | Jacobsen et al. |
| 2008/0021404 A1 | 1/2008 | Jacobsen et al. |
| 2008/0021405 A1 | 1/2008 | Jacobsen et al. |
| 2008/0021406 A1 | 1/2008 | Jacobsen et al. |
| 2008/0021408 A1 | 1/2008 | Jacobsen et al. |
| 2008/0077119 A1 | 3/2008 | Snyder et al. |

FOREIGN PATENT DOCUMENTS

| | | |
|---|---|---|
| AU | 7338966 | 4/1998 |
| BR | 9712829 | 1/2000 |
| CA | 2266685 | 5/2006 |
| CA | 2255781 | 3/2007 |
| CN | 1230914 | 10/1999 |
| DE | 2539191 | 3/1976 |
| DE | 285514 | 12/1990 |
| EP | 0 045 931 | 2/1982 |
| EP | 0 069 522 | 1/1983 |
| EP | 0 087 933 | 9/1983 |
| EP | 0 111 044 | 6/1984 |
| EP | 0 181 174 | 5/1986 |
| EP | 0377453 | 7/1990 |
| EP | 0 565 065 | 6/1996 |
| EP | 0 778 038 | 6/1997 |
| EP | 0 778 039 | 6/1997 |
| EP | 0 778 040 | 6/1997 |
| EP | 0 812 599 | 12/1997 |
| EP | 0 865 772 | 9/1998 |
| EP | 0 865 773 | 9/1998 |
| EP | 0 521 595 | 5/1999 |
| EP | 0 917 885 | 5/1999 |
| EP | 0 937 481 | 8/1999 |
| EP | 0 790 066 | 4/2000 |
| EP | 0 608 853 | 4/2003 |
| EP | 0 935 947 | 12/2004 |
| EP | 0 934 141 | 11/2005 |
| GB | 2214354 | 8/1989 |
| GB | 2257269 | 1/1993 |
| JP | 58-8522 | 1/1983 |
| JP | 60091858 | 5/1985 |
| JP | 61022752 | 1/1986 |
| JP | 62023361 | 1/1987 |
| JP | 62089470 | 4/1987 |
| JP | 62299277 | 12/1987 |
| JP | 6393516 | 4/1988 |
| JP | 63-181774 | 7/1988 |
| JP | 63217966 | 9/1988 |
| JP | 1089956 | 4/1989 |
| JP | 1135363 | 5/1989 |
| JP | 1158936 | 6/1989 |
| JP | 2107268 | 4/1990 |
| JP | 3081831 | 4/1991 |
| JP | 03-122850 | 12/1991 |
| JP | 4061840 | 2/1992 |
| JP | 4099963 | 3/1992 |
| JP | 4213069 | 8/1992 |
| JP | 4213070 | 8/1992 |
| JP | 4236965 | 8/1992 |
| JP | 5149969 | 6/1993 |
| JP | 5-506806 | 10/1993 |
| JP | 5-309159 | 11/1993 |
| JP | 5-507857 | 11/1993 |
| JP | 6-501179 | 2/1994 |
| JP | 631749 | 4/1994 |
| JP | 6169996 | 6/1994 |
| JP | 6-63224 | 9/1994 |
| JP | 6312313 | 11/1994 |
| JP | 728562 | 5/1995 |
| JP | 7124164 | 5/1995 |
| JP | 7124263 | 5/1995 |
| JP | 7136280 | 5/1995 |
| JP | 7148264 | 6/1995 |
| JP | 7505561 | 6/1995 |
| JP | 7037199 | 7/1995 |
| JP | 7185009 | 7/1995 |
| JP | 7255855 | 10/1995 |
| JP | 7275366 | 10/1995 |
| JP | 751067 | 11/1995 |
| JP | 8-229888 | 9/1996 |
| JP | 8229888 | 9/1996 |
| JP | 8509141 | 10/1996 |
| JP | 8317988 | 12/1996 |
| JP | 9000164 | 4/1997 |
| JP | 9-276413 | 10/1997 |
| JP | 9276413 | 10/1997 |
| JP | 9-294813 A | 11/1997 |
| JP | 9294813 | 11/1997 |
| JP | 10-118193 | 5/1998 |
| JP | 10-305039 | 11/1998 |
| JP | 10305039 | 11/1998 |
| JP | 10328191 | 12/1998 |
| JP | 11-226131 A | 8/1999 |
| JP | 11-267224 A | 10/1999 |
| JP | 2000-197704 A | 7/2000 |
| JP | 2000-510722 A | 8/2000 |
| JP | 2000-511083 A | 8/2000 |
| JP | 2001-500808 A | 1/2001 |
| JP | 2002-529137 A | 9/2002 |
| JP | 2002-542901 A | 12/2002 |
| JP | 2002-543896 A | 12/2002 |
| JP | 2003-517893 A | 6/2003 |
| JP | 3649604 | 2/2005 |
| JP | 2005-534407 | 11/2005 |
| SU | 712908 | 1/1980 |
| SU | 758421 | 8/1980 |
| SU | 1529365 | 12/1989 |
| WO | WO 90/02520 | 3/1990 |
| WO | WO 91/13364 | 9/1991 |
| WO | WO 92/04072 | 3/1992 |
| WO | WO 92/07619 | 5/1992 |
| WO | WO 93/04722 | 3/1993 |
| WO | WO 93/11313 | 6/1993 |
| WO | WO 95/24236 | 9/1995 |
| WO | WO 96/19255 | 6/1996 |
| WO | WO 97/10022 | 3/1997 |
| WO | WO 97/25914 | 7/1997 |
| WO | WO 97/43949 | 11/1997 |
| WO | WO 97/44083 | 11/1997 |
| WO | WO 97/44086 | 11/1997 |
| WO | WO 98/10694 | 3/1998 |
| WO | WO 99/04847 | 2/1999 |
| WO | WO 99/11313 | 3/1999 |
| WO | WO 00/27303 | 5/2000 |
| WO | WO 00/30710 | 6/2000 |
| WO | WO 00/48645 | 8/2000 |
| WO | WO 00/57943 | 10/2000 |
| WO | WO 00/66199 | 11/2000 |
| WO | WO 00/67845 | 11/2000 |
| WO | WO 00/72907 | 12/2000 |
| WO | WO 01/28620 | 4/2001 |
| WO | WO 01/36034 | 5/2001 |
| WO | 0145912 | 6/2001 |
| WO | WO 01/45773 | 6/2001 |
| WO | WO 01/93920 | 12/2001 |
| WO | WO 02/13682 | 2/2002 |
| WO | WO 02/062540 | 8/2002 |
| WO | WO 03/004086 | 1/2003 |
| WO | WO 03/008148 | 1/2003 |
| WO | WO 2004/012804 | 2/2004 |
| WO | 2004047899 | 6/2004 |

\* cited by examiner

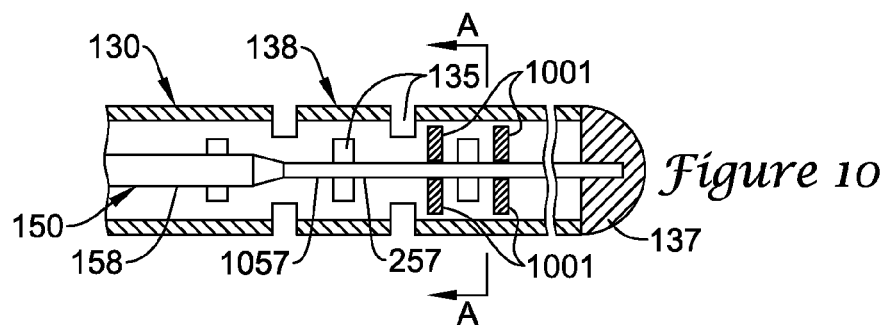
Figure 10
Figure 10A
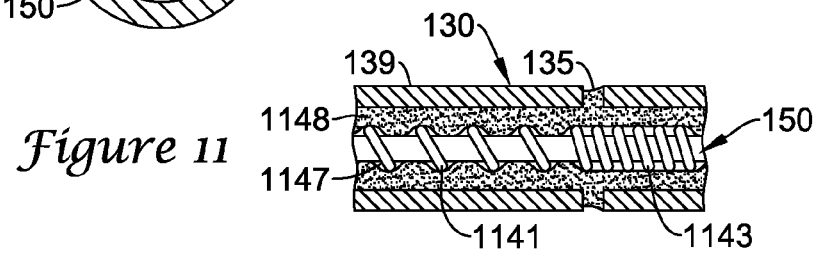
Figure 11
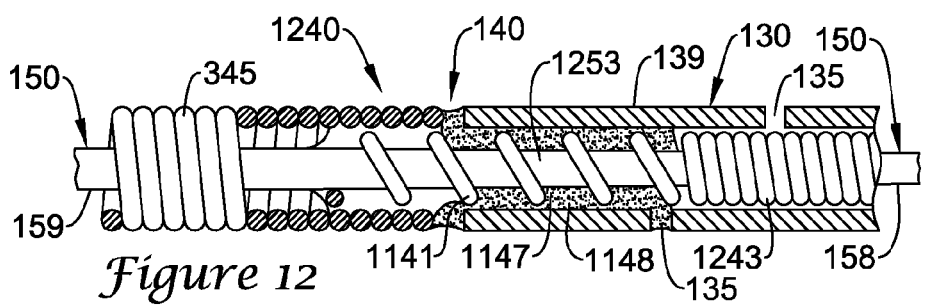
Figure 12
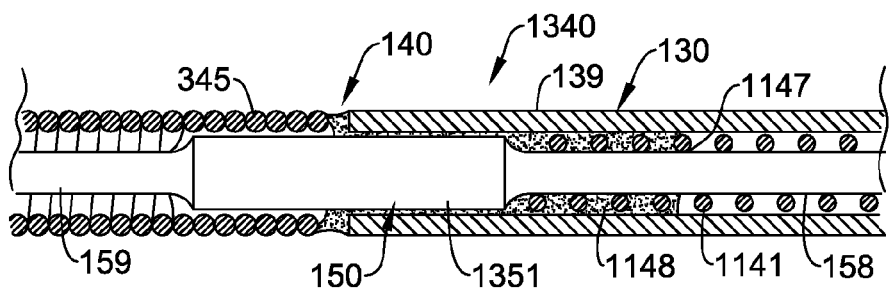
Figure 13

MEDICAL DEVICE FOR NAVIGATION THROUGH ANATOMY AND METHOD OF MAKING SAME

CROSS REFERENCE TO RELATED APPLICATIONS

This application is a continuation of U.S. patent application Ser. No. 10/604,504 filed Jul. 25, 2003, now U.S. Patent Publication No. US 2004/0181174 A2, which claims the benefit of priority to U.S. Provisional Application No. 60/399,046, filed Jul. 25, 2002, the entire disclosures of which are all hereby incorporated by reference.

FIELD OF INVENTION

This invention relates generally to medical devices for navigating through anatomy and methods of making them.

BACKGROUND OF INVENTION

Medical devices, such as endovascular or intravascular devices, have been used for many years for purposes such as performing various medical procedures. A medical device such as an intravascular device may be introduced into a patient's anatomy or vasculature at a relatively accessible location, and guided through the patient's anatomy to the desired location. X-ray fluoroscopy has been used to observe the tip of the medical device and the device has been rotated at bifurcations in the anatomy or vasculature before being pushed further to guide the device to the desired target location. Medical devices of this type may be solid, for example, a guidewire, or may be hollow and tubular, for example, a catheter. Guidewires may be used to guide one or more tubular intravascular devices to a particular location, and catheters may be used, for instance, to deliver fluids, extract fluids, or deliver various objects, agents, or devices to the particular location.

In many applications it is desirable that a medical device or intravascular device bend easily in order to allow it to make the various bends and turns that are necessary to navigate through the anatomy or vasculature, and in some cases also to minimize trauma to the anatomy or vasculature. However, in many applications it is also desirable that the medical device is stiff enough to not prolapse, for example, when navigating through relatively large vasculature. It may also be desirable that such medical devices be relatively stiff in torsion in order to allow precise control of rotation in order to guide the device through bifurcations in vasculature or around obstacles. Another desirable feature of many embodiments is that they minimize friction with the anatomy to facilitate their insertion, removal, or both. It may also be desirable for these medical devices to have adequate radiopacity, particularly at the distal end, to make them observable under X-ray fluoroscopy for purposes of navigation.

In addition, it is desirable that medical devices, such as guidewires, are strong and durable enough to assure their complete removal from the patient. Thus, it is desirable that such devices have adequate tensile strength and resist fatigue during use. Further, where expensive materials such as nitinol are used, or expensive fabrication techniques such as forming many slots, it is desirable that the quantity of these materials or techniques be limited to locations where they are actually needed in order to make the devices as inexpensive to manufacture as possible. Other features and benefits are also desirable, at least some of which are described herein or are apparent from this document.

SUMMARY OF INVENTION

The present invention provides medical devices including intravascular devices such as guidewires. Features of various embodiments of the present invention include that the devices provide the desired flexibility in bending, provide excellent stiffness in torsion, reduce friction with the anatomy, provide better radiopacity than the prior art, particularly at the distal end, resist fatigue, minimize trauma to the patient's anatomy, are capable of navigating through tortuous vasculature, provide the necessary tensile strength to assure complete removal of the medical device, and are inexpensive to manufacture. Other features and benefits are described herein or are apparent from this document, including features and benefits for particular embodiments of the present invention.

Accordingly, the present invention provides a medical device for navigation through anatomy having an elongate body with a proximal end, a distal end, and a longitudinal axis extending at least from the proximal end to the distal end. Such a medical device may include a helical coil formed from wire having a substantially non-circular cross section, and the cross section may have a greater dimension in the radial direction than in the axial direction. The body may include a tubular member with a plurality of slots, which may be configured to make the body or tubular member more flexible in bending. The coil may be located at or near the distal end of the tubular member, and may be made of a substantially radiopaque material. The body may further have a core wire, and at least part of the core wire may be located inside the tubular member, inside the coil, or both. Such a medical device may be a guidewire, for example.

The present invention also provides a medical device configured to be guided to a target location in anatomy, having a tubular member and a core wire extending proximally from the tubular member and attached there with a joint. This joint may have a coil circumscribing the core wire, and at least partially inside the tubular member, and may utilize solder, adhesive, or both. For instance, the core wire and the coil may be metal, and the joint may have solder attaching the coil to the core wire and adhesive attaching the coil, solder, core wire, or a combination thereof, to the tubular member. To allow room for solder, adhesive, or both between the windings, at least a portion of the coil may have a pitch of at least 1.5 times the diameter of the coil wire.

In some embodiments, the core wire may have a tapered portion, and the joint may be located at least partially within the tapered portion. And in some embodiments, the core wire may have a feature configured to facilitate mechanical interlock of the solder or adhesive, and the joint may be located at that feature. Such a feature may include, for example, a step, a ridge, or both. Thus, in some embodiments of the present invention, the core wire may have at least one abrupt change in cross-sectional dimension, for example, between its proximal and distal sections. The core wire may be attached to the tubular member with the proximal end of the tubular member abutting the abrupt change in cross-sectional dimension or abutting a proximal coil attached to the core wire. There may be a smaller diameter mesial coil circumscribing at least a portion of the core wire, which may be soldered to the core wire, and the tubular member may be attached to the mesial coil, for example, with adhesive. And in various embodiments, the core wire may further be attached to the tubular member at the distal end of the tubular member, at one or more locations intermediate the proximal end and the distal end, or both.

In some embodiments of the present invention, the core wire may generally have a substantially round cross section, but a distal section of the core wire located inside the tubular member may have a flattened cross section for at least a portion of its length. Such an embodiment may have substantially radiopaque material located inside the tubular member at the distal section or end, which may have a substantially semicircular cross section and may be located on opposite sides of the flattened cross section of the core wire.

In some embodiments of the present invention, there may be a coil extending distally from the distal end of the tubular member. Such a coil may be made of a substantially radiopaque material, and there may be a mesial coil of another material proximal to the radiopaque coil. The core wire may extend distal to the tubular member inside the coil, and may attach at the distal end of the coil, core wire, or both. In such embodiments, the core wire may be axially but not torsionally constrained relative to the coil at the distal tip of the core wire.

In other embodiments of the present invention, the tubular member may extend distal to the distal tip of the core wire and the medical device may have at least one piece of radiopaque material inside the tubular member, at or adjacent to the distal end of the tubular member, and distal to the distal tip of the core wire. In such embodiments, the core wire may be attached to the tubular member at the distal tip of the core wire. The radiopaque material may be in the shape of a helical coil, for example. In some embodiments, the tubular member may have superelastic properties, and at least part of the distal end may be heat treated to reduce its superelastic properties, for example, to make it shapeable by the user. And in some embodiments, the tubular member may have a chamfer at its proximal end.

The present invention still further provides embodiments having a tapered body, at least in its outside diameter over at least a portion of its length. The taper may have a decreasing outside diameter in the distal direction, and may be either continuous or incremental. In some embodiments, the core wire may have a larger outside diameter along at least a majority of its proximal section than that of the tubular member. But in some embodiments, the tapered portion may include the tubular member. In an incrementally tapered embodiment of the tubular member, the tubular member may have an outside diameter that changes in at least one step between the proximal end and the distal end. In some such embodiments, the tubular member may have a plurality of sections which may have different outside diameters, and the sections may be attached to each other to form the tubular member.

Various embodiments of the tubular member include a plurality of groups of slots formed therein, which may be substantially perpendicular to the axis, and these groups may include a plurality of slots at substantially the same location along the axis. At least a plurality of the longitudinally adjacent groups of slots may be rotated at an angle around the axis from the previous group, and the angle may be in the range of 180 degrees plus or minus no more than 40 degrees, that quantity divided by the number of slots in the group. In some embodiments, at least a plurality of the groups may have at least three slots or may consist of precisely three slots. In such embodiments, the angle of rotation between adjacent groups may be 180 degrees divided by the number of slots in the group, plus or minus no more than 10 degrees.

In some embodiments, each slot in at least a plurality of the groups may be substantially equal in size and equally spaced around the axis. But in some embodiments, in at least some groups, at least one slot may be substantially deeper than at least one other slot. In such embodiments, the medical device may be configured so that tensioning the core wire causes the distal end of the tubular member to change in shape, such as bending or changing the angle of bend. In addition, in some embodiments, the spacing between adjacent groups of slots may vary gradually or incrementally along at least part of the tubular member providing a varying bending stiffness along that distance, and these groups may be more closely spaced at the distal end.

Further, some embodiments of the present invention may have another tubular member. Thus, some embodiments of the present invention may have two tubular members which may share a common longitudinal axis, and may be attached to each other, to the core wire, or both. One or both tubular members may circumscribe at least a portion of the core wire, and the two tubular members may be concentric or in line with each other. One or both tubular members may have a plurality of slots configured to make it more flexible in bending, but one or both tubular members may also have a portion without slots, which may be proximal to the portion with slots. In some embodiments, one tubular member may lack slots altogether, and may be made of a polymer material. In some embodiments, one tubular member may be made of a substantially radiopaque material. There may also be at least one coil concentric with at least one of the tubular members, the core wire, or a combination thereof. One coil may be inside at least one of the tubular members, and some embodiments may have at least one coil circumscribing the core wire. At least one tubular member may be at least partially located inside a coil. Such coils may be used in joints, provide additional bending stiffness, or provide a greater or smoother outside diameter, for example.

BRIEF DESCRIPTION OF DRAWINGS

The figures in this document illustrate various exemplary embodiments of the present invention. Embodiments of the present invention may include part or all of the features shown in one of these drawings, or may include features from two or more figures. Embodiments of the present invention may also include features described in the specification, or limitations to features described in the specification. Furthermore, embodiments of the present invention may include features that would be familiar to a person of ordinary skill in the art having studied this document.

FIG. 10 is a cross-sectional side view illustrating the distal end of an embodiment of a medical device in accordance with the present invention having a core wire with a flattened distal end;

FIG. 11 is a partially cross-sectional side view illustrating an embodiment of a mesial joint in accordance with the present invention having a coil around a core wire and inside a tubular member;

FIG. 12 is a partially cross-sectional side view illustrating an embodiment of a mesial joint in accordance with the present invention having at least two coils around a core wire at least one located at least partially inside a tubular member;

FIG. 13 is a partially cross-sectional side view illustrating an embodiment of a mesial joint in accordance with the present invention having two coils and a core wire with a ridge forming an abrupt change in diameter;

DETAILED DESCRIPTION

The present invention provides medical devices and intravascular devices such as guidewires and catheters, improvements to such devices, and methods of making these devices. Included in the present invention are various embodiments providing substantially radiopaque material at or near the distal end to facilitate X-ray fluoroscopy including edge-wound coils, and substantially radiopaque material located inside a tubular member, which may be slotted to improve its bending flexibility. The present invention also includes various embodiments of flexible distal tips including extended coil tips, and tips with a flattened core wire. The present invention even further includes various embodiments of a mesial joint between a core wire and tubular member. Many such embodiments use a coil between the core wire and proximal end of the tubular member, and solder, adhesive, or both. The present invention still further includes various embodiments of medical devices with a coil or second tubular member sharing a common longitudinal axis with the first tubular member, which may reduce the necessary length of the first tubular member, provide radiopacity, reduce friction, seal the slots, provide better bending flexibility, or a combination of these benefits. The present invention also includes embodiments of various geometry of slots formed in a tubular member, including arrangements of slots in groups of two, three, or more, and geometries wherein different slots in at least some groups are unequal in depth. These later embodiments provide a steerable device. The present invention also provides embodiments having tapered bodies, which may include tapered tubular members.

Figure 1:
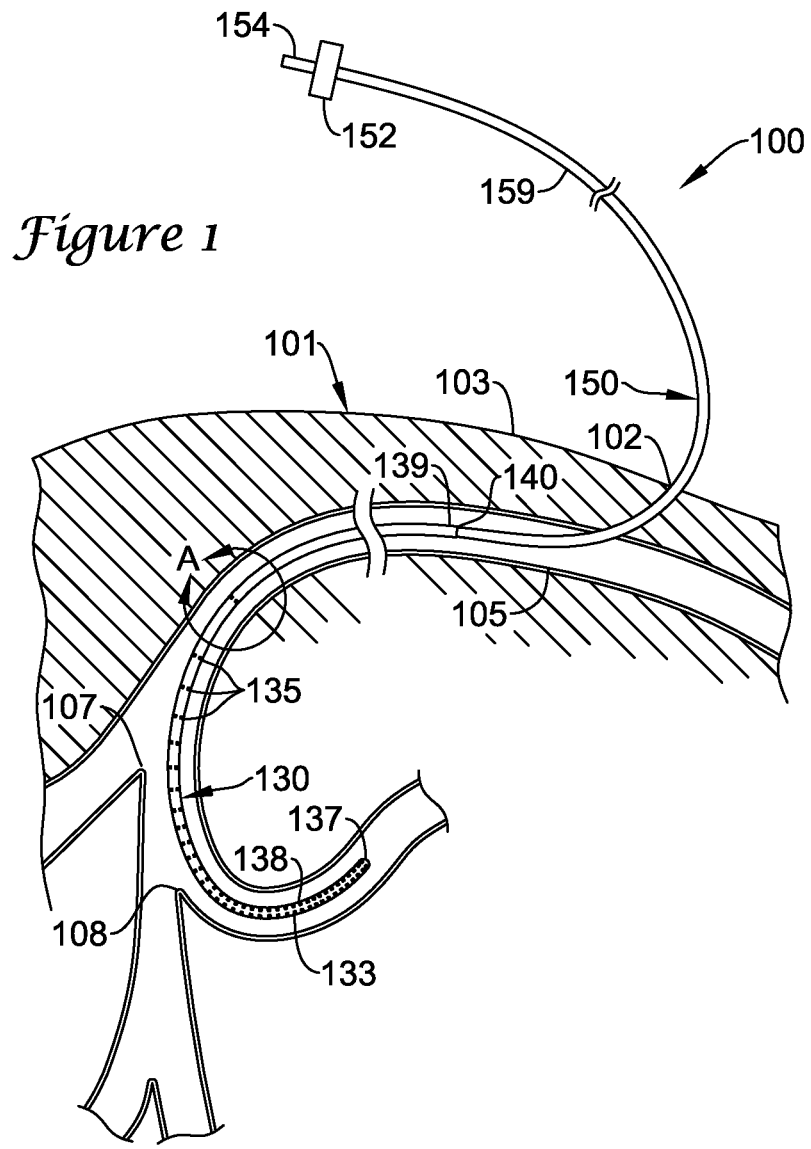
FIG. 1 is a partially cross-sectional side view illustrating an embodiment of a medical device in accordance with the present invention inserted in vasculature in anatomy.
Figure 1A:
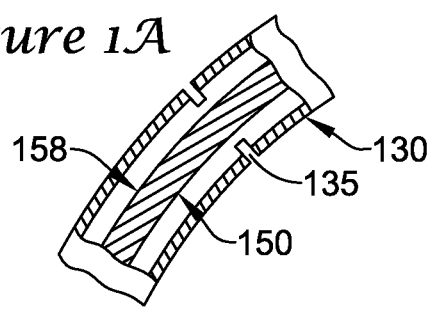
FIG. 1A is a detail cross-sectional side view of part of the embodiment illustrated in FIG. 1.

Accordingly, FIG. 1 illustrates an exemplary embodiment of the present invention, guidewire 100. Use as a guidewire is one example of a use or function of a medical device in accordance with the present invention. Various elements of the present invention may be used for other purposes including various medical purposes. Guidewire 100 may include tubular member 130 and core wire 150, which may be attached to each other, for example, at joint 140. Tubular member 130, core wire 150, or both, may form an elongate body of guidewire 100, which may have a common axis through its length from at least the proximal end to the distal end. In other words, tubular member 130 and core wire 150 may share a common longitudinal axis. As used herein, components are said to share a longitudinal axis if they are coaxial or in line. The body of guidewire 100 may have a proximal end 154 and a distal end 138 or tip 137. This body may include an elongate section 159 proximal to joint 140 and an elongate section distal to joint 140. The distal elongate section may include tubular member 130 distal section 158 of core wire 150, or both, for example. Tubular member 130 may have distal end 138 and proximal end 139. Distal end 138 may include distal tip 137 of guidewire 100, which may be rounded as shown. Joint 140 is at proximal end 139 of tubular member 130, in the exemplary embodiment illustrated.

Core wire 150 may extend proximally from tubular member 130 (e.g. from proximal end 139 or joint 140 as shown). Core wire 150 may also extend distally from joint 140 inside tubular member 130 as shown. Core wire 150 may have a circular cross section, and may have a proximal section 159, which may have a constant outside diameter along part or all of its length, and a distal section 158, which may have a smaller diameter than proximal section 159. In some embodiments, proximal section 159 may have a substantially constant diameter along a majority of its length. In some embodiments, proximal section 159, distal section 158, portions thereof, or a combination of these, may be tapered with a decreasing diameter toward distal tip 137. Distal section 158 of core wire 150 may be located at least partially inside tubular member 130 as shown. In various embodiments, tubular member 130 may have an outside diameter that is smaller, larger, or the same size as proximal section 159 of core wire 150. The outside diameter of tubular member 130 may be substantially constant along all or a majority of its length, or may be tapered, exemplary embodiments of which are described below. Similarly, the inside diameter of tubular member 130, and the wall thickness, may be substantially constant along the length of tubular member 130, or may be tapered.

Guidewire 100 may be configured to be flexible in bending, particularly near distal end 138. The bending stiffness of guidewire 100 may gradually or incrementally decrease along guidewire 100 toward distal tip 137, or along a portion of guidewire 100. For example, the bending stiffness may be constant along proximal section 159 of core wire 150, but may decrease gradually along distal section 158 or tubular member 130, for instance, from proximal end 139 to distal end 138. This flexibility may be accomplished, at least in part, with a plurality of slots 135 formed in at least part of tubular member 130 as shown in several figures including FIG. 1. Slots 135 may be micromachined into tubular member 130, and may be configured to make tubular member 130 more flexible in bending. To provide a change in bending stiffness along the length of tubular member 130, slots 135 may be closer together, deeper, or wider, near distal end 138, in comparison with proximal end 139. In some embodiments, proximal end 139 of tubular member 130 may have no slots 135, as shown in FIG. 1. In other embodiments, proximal end 139 may contain slots 135, but they may be farther apart than at proximal end 138, for example. This spacing may vary gradually along tubular member 130, or may change incrementally. In many embodiments, slots 135 may actually be closer together than what is shown in FIG. 1.

In some embodiments, the stiffness of all or part of core wire 150 (for example, distal section 158) may also change along its length by reducing in dimension or diameter. In some embodiments, varying flexibility along guidewire 100 may be accomplished or aided by using materials with different properties at different locations. In some embodiments, more flexible materials may be used at the distal end, while stiffer materials may be used at the proximal end. In some embodiments, more flexible materials may be used at the outside surface farther from the longitudinal axis, while stiffer materials may be used in the center or near the axis. Different components made of two or more different materials having different elasticity may be joined with joints. For example, tubular member 130 may be made of a superelastic material such as nitinol, to allow it to bend more without yielding or fatiguing. In comparison, core wire 150 may be made of a stiffer material having a greater modulus of elasticity, for example, stainless steel. As used herein, materials that have two percent recoverable strain, or more, are considered to be superelastic materials and have superelastic properties. Nitinol, for example, may have a recoverable strain of up to ten percent, depending on the chemistry, heat treatment, and the like. Nitinol having a recoverable strain of at least two percent is considered herein to be superelastic.

In embodiments wherein tubular member 130 is made of a superelastic material and core wire 150 is made of a stiffer or more common material such as stainless steel, there may be various advantages to using more of one component than the other, or relying on one component rather than the other to provide various properties such as is bending stiffness. For instance, a stainless steel core wire 150 may have a lower material cost than superelastic nitinol tubular member 130. In addition, it may be expensive to form slots 135 in tubular member 130. Thus, there may be a cost benefit to minimizing the length of tubular member 130. In addition, slots 135 may substantially reduce the tensile strength of tubular member 130. Therefore, it may be an advantage for core wire 150 to be as large as possible to provide adequate tensile strength when the medical device is removed. On the other hand, due to its superelastic properties, tubular member 130 may be able to bend or twist more without failing or deforming plastically. In addition, due to its shape or cross section, slotted tubular member 130 may provide a greater torsional stiffness relative to its bending stiffness, than core wire 150, thus providing greater rotational control of distal tip 137 from chuck 152. Thus, there may also be advantages to having a relatively long tubular member 130, or using tubular member 130 to provide bending stiffness rather than distal section 158 of core wire 150.

As an example, some embodiments of the present invention may have a proximal end 139 of tubular member 130 without slots 135 (illustrated, for example, in FIGS. 1, 20, and 24), whereas other embodiments of the present invention may have a shorter tubular member 130 omitting a proximal end 139 without slots 135 (illustrated, for example in FIG. 3), and providing the desired bending stiffness in this area with a larger diameter of core wire 150. The first such type of embodiments may be more expensive to make (assuming tubular member 130 is longer), but may be able to bend more sharply at unslotted proximal end 139 of tubular member 130 without undergoing plastic deformation or experiencing fatigue. The first such type of embodiments may also be stiffer in torsion at that location. In this example, the first type of embodiments may provide adequate tensile strength at unslotted proximal end 139, since there are no slots reducing the tensile strength of proximal end 139. Further, it may be beneficial to attach tubular member 130 to core wire 150 at the distal end of the unslotted portion. Both such types of embodiments are described in more detail below.

Guidewire 100 is shown in FIG. 1 navigating through anatomy 101. Specifically, guidewire 100 is shown penetrating through an opening 102 that has been cut into the surface of skin 103 and into vasculature 105. Guidewire 100 is shown passing a distance through vasculature 105, including through two bifurcations 107 and 108. Distal end 138 may include bend 133, which may facilitate navigating guidewire 100, for example, through the desired branch of bifurcations 107 and 108. Core wire 150 may contain a handle or chuck 152, which may be attached or clamped to proximal end 154 or proximal section 159 of core wire 150, and may be manipulated to rotate guidewire 100 about its axis. For instance, guidewire 100 may be manually rotated as it is advanced through vasculature 105 to select the desired passageways, for example, at bifurcations 107 and 108.

Accordingly, it is generally desirable that embodiments of the present invention move easily through anatomy 101. Various features and components are described herein which may facilitate such movement, for example, by reducing friction between guidewire 100 and anatomy 101. For instance, all or part of various embodiments of the present invention including guidewire 100 may be coated on its exterior surface with a lubricious coating or lubricant. As examples, guidewire 100 may be coated with a PTFE, Parylene, hydrophilic, or hydrophobic coating.

In some embodiments of the present invention, the tip or distal end 138 is constructed with a particular preformed bend 133. In embodiments having a distal end 138 made of a superelastic material, it may be difficult or impossible for a user to change bend 133. One reason for this may be that the superelastic material of tubular member 130, core wire 150, or both cannot be bent sharply enough to take a permanent set. Accordingly, embodiments of the present invention include a method for making a medical device or guidewire 100 that includes locally reducing the superelastic properties in the tip or distal end 138 of the medical device or guidewire 100, enough that the tip or distal end 138 can be shaped by bending it around a tight radius.

This may be done, for example, by first forming the medical device, at least part from a superelastic material such as nitinol, and then heat treating or annealing the part of the tip or distal end 138 that is desired to be shapeable. An example of such a cycle consists of heating the tip or distal end 138 to approximately 600 degrees C. for 10 seconds. The result may be a reduction in the superelastic effect in the heat treated zone which may provide the ability to achieve a permanent set or bend 133 in the material of distal end 138 when it is bent sharply.

A user of such a medical device or guidewire 100 with a shapeable tip, such a doctor or surgeon, may determine the optimal angle and location of bend 133, for example, from the type of procedure to be performed, the anatomy of the particular patient (e.g., the geometry of bifurcations 107 and 108), or both. The user may then bend tip 133, and proceed to insert guidewire 100 into opening 102 of anatomy 101 and into vasculature 105, and to observe distal end 138 of guidewire 100 with x-ray fluoroscopy, for example, while navigating guidewire 100 through vasculature 105. In some embodiments, magnetic resonance imaging (MRI) may be used for observation instead or in addition. At bifurcations 107 and 108, the user may rotate chuck 152 to turn bend 133 to point distal tip 137 toward the desired direction and advance guidewire 100 to the target location. Once at the target location, the user may perform a medical procedure or advance a catheter over guidewire 100 to that location to perform a procedure. When the procedure is completed, or when the catheter is installed, the user may pull guidewire 100 out through opening 102.

The present invention includes techniques for construction and embodiments of small diameter guidewires 100. Various embodiments of the present invention may be advantageous, for example, in medical devices having small diameters (for example, outside diameter (OD) of the guidewire <0.014"). In such embodiments, the outer diameter of proximal section 159 of core wire 150 proximal to tubular member 130 may be larger than the outer diameter of tubular member 130. This may give proximal section 159 of core wire 150 more torsional stiffness, but this may be at the expense of greater bending stiffness. In many applications, the greater bending stiffness may not be a problem for small diameter guidewires 100 because the tortuosity of the anatomy (e.g., of vasculature 105) that the proximal section 159 of core wire 150 must traverse may be low enough to permit greater bending stiffness.

In some embodiments of the present invention, including small-diameter guidewires 100, it may be beneficial to have a relatively-stiff (in bending) portion of guidewire 100 proximal to distal end 138. Relatively-high stiffness in this area may prevent prolapsing when guidewire 100 is being advanced in relatively-large vessels 105, and may facilitate catheter tracking where a sharp branch is negotiated off a relatively-large vessel 105. This relatively-stiff portion may be created, for example, by spacing slots 135 further apart in this relatively-stiff portion of tubular member 130. As an example, guidewire 100 may be constructed with a bending stiffness of approximately 0.00005 pound inches squared ($lb-in^2$) for the first one half centimeter (cm) of length from distal tip 137, followed by a gradual increase in stiffness to 0.0002 $lb-in^2$ one cm from distal tip 137. The stiffness may then remain constant until about four cm from distal tip 137, at which location the stiffness may decrease gradually to about 0.0001 $lb-in^2$ five cm from distal tip 137. The stiffness may then remain constant until about eight cm from distal tip 137, at which location the stiffness may increase gradually to about 0.0004 $lb-in^2$ approximately twenty cm from distal tip 137. The bending stiffness may then remain substantially constant (e.g., along proximal section 159 of guidewire 100).

Figure 2:
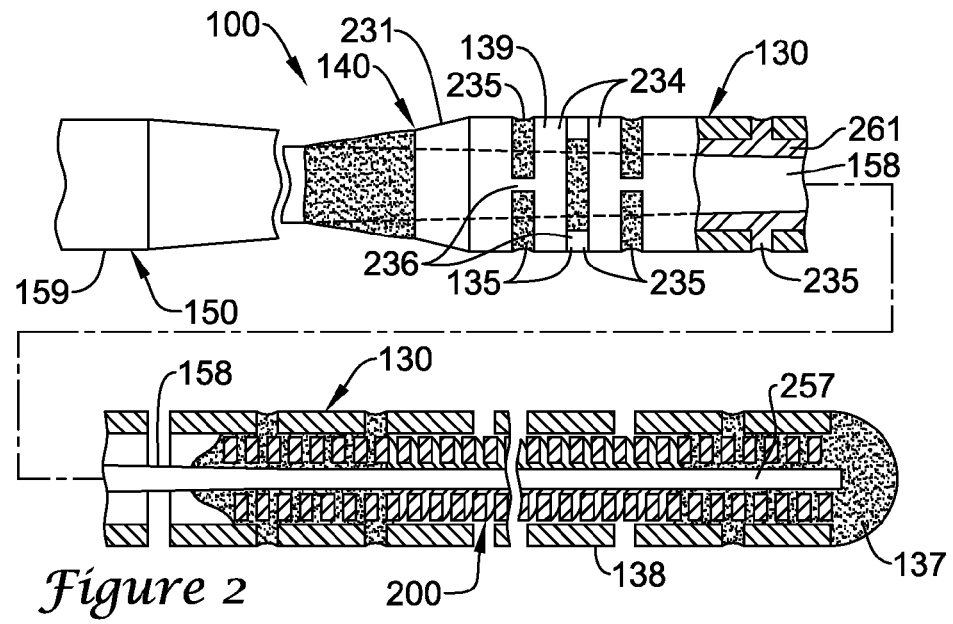
FIG. 2 is a partially cross-sectional side view illustrating a mid-portion and distal end of an embodiment of a medical device in accordance with the present invention having a coil inside a slotted tubular member.

In a variety of embodiments, medical devices in accordance with the present invention, including guidewire 100, may have a dense material in distal end 138 or tip 137, for example, to make the end or tip more easily observable under x-ray fluoroscopy. An exemplary embodiment of a guidewire 100 with a substantially radiopaque coil 200 is illustrated in FIG. 2. This embodiment of guidewire 100 utilizes a micromachined or slotted nitinol torque tube or tubular member 130 surrounding section 158 of core wire 150. Marker coil 200 may lie inside tubular member 130 at or near distal end 138, and may circumscribe or surround distal end 257 of core wire 150. The helical coil shape of coil 200 may allow distal end 138 to remain flexible in bending, while tubular member 130 may maintain relative torsional stiffness of guidewire 100 to tip 137. Coil 200 may be made of a dense material such as, for example, a platinum-tungsten or platinum-iridium alloy to achieve adequate radiopacity for distal end 138. Such metals are "substantially radiopaque", as that phrase is used herein. In general, materials having substantially more radiopacity than stainless steel or nitinol are considered herein to be substantially radiopaque. Some embodiments of the present invention may have a coil 200 that is not made of a substantially radiopaque material. Such a helical coil 200 may, for example, contribute to the bending stiffness of the device, center core wire 150, facilitate bonding between other components, or a combination of these functions.

One problem to be overcome in small diameter guidewires is providing adequate radiopacity. In order to increase the radiopacity coil 200 to a required or desired level, the diameter of the platinum or tungsten wire may be increased. But because the annular space between core wire 150 and the inner diameter of the micromachined tubular member 130 may be small, there may not be enough space to provide an adequately radiopaque coil 200 between core wire 150 and tubular member 130. In addition, increasing the diameter of the wire used to wind marker coil 200 may have the undesired effect of increasing the bending stiffness of marker coil 200. Several approaches in accordance with the present invention may be used to overcome this problem.

Figure 3:
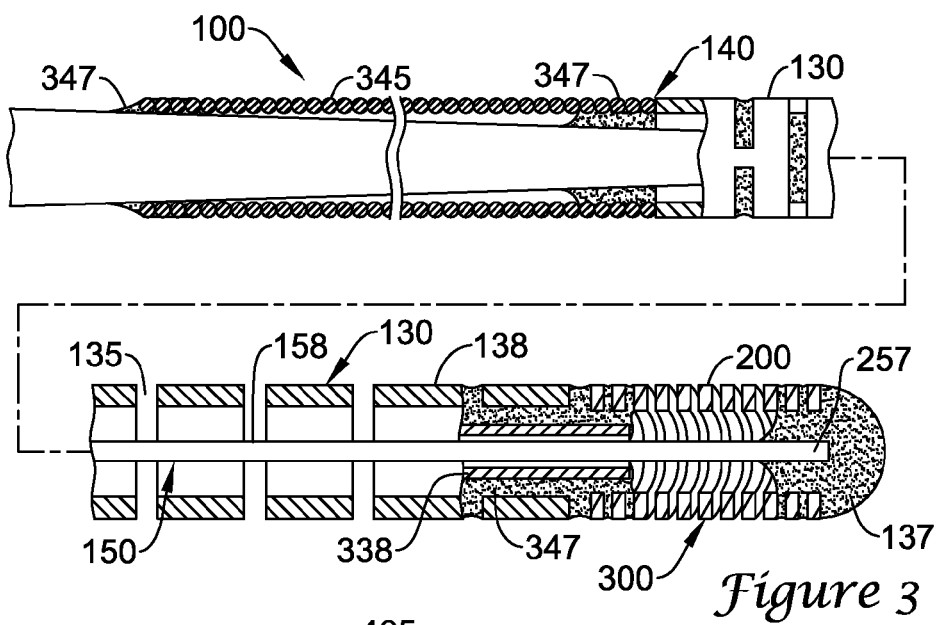
FIG. 3 is a partially cross-sectional side view illustrating a mid-portion and distal end of an embodiment of a medical device in accordance with the present invention having an extended coil tip.

In an exemplary embodiment illustrated in FIG. 3, helical coil 200 is larger in diameter than coil 200 shown in FIG. 2, and extends beyond distal end 138 of tubular member 130 rather than being located inside tubular member 130. Thus, FIG. 3 illustrates an exemplary embodiment of the present invention having an extended coil tip 300. Section 158 of core wire 150 may provide the desired stiffness in bending and torsion, and may provide tensile strength. Coil 200 may contribute to the stiffness of extended coil tip 300, especially in bending. In some embodiments, coil 200 may provide all of the bending stiffness of extended coil tip 300. Some such embodiments may lack core wire 150, at least within part of or all of extended coil tip 300.

Helical coil 200 may be attached to distal end 138 of tubular member 130, and may extend distally therefrom, for example, to distal tip 137. Extended coil tip 300 may provide radiopacity, an atraumatic diameter to contact the anatomy that is significantly larger in diameter than core wire 150, or both. An extended coil tip 300 having helical marker coil 200 illustrated in FIG. 3, may be used, for example, in a 0.014-inch OD coronary guidewire. The length of extended coil tip 300 or coil 200 may range, for example, from 0.5 to 5 cm.

In some embodiments of the present invention, coil 200 may be wound from wire having a round or circular cross section. But other embodiments, wire with a non-circular or substantially non-circular cross section may be used. In some embodiments, such a non-circular cross section may have at least one flat side, or two, three, or four flat sides, for example. As illustrated in FIGS. 2-5, coil 200 may be formed from an edge wound strip, which may give coil 200 a high degree of bending flexibility, greater radiopacity, or both. Thus, the cross section of the wire from which coil 200 is made, may have a greater dimension in the radial direction than in the axial direction (i.e., relative to the longitudinal axis). Edge wound coil 200 may also provide improved torsional stiffness, strength, or both, when compared with other embodiments.

The edge-wound flat, trapezoidal, or rectangular cross-section illustrated for coil 200 allows the construction of a coil 200 with a higher radiopacity (density), a lower bending stiffness, or both, in comparison with a coil 200 wound from round wire. This is because when a strip is wound on edge to form coil 200 (i.e., has a greater dimension in the radial direction than in the axial direction) it may result in a lower stiffness, and a greater density (and hence radiopacity), or both, when compared to a coil with the same inside diameter (ID) and outside diameter (OD) wound from round wire. Specifically, a rectangular strip coil 200 may have, for example, about $1/7^{th}$ of the lateral stiffness and $1/3$ more density, when compared with a round wire coil 200. The increase in density generally stems from better utilization of space. The stiffness may be decreased because there are more turns of a less stiff wire in a given length of the rectangular wire coil 200 than in the same length on round wire coil 200. For instance, coil 200 may have a 0.003-inch ID and a 0.009-inch OD. When made of a round wire, with a diameter of 0.003 inches, coil 200 may have a 0.005-inch pitch, a lateral stiffness of 20 ($in^2$-lbs), and a density of 9 g/in. In comparison, a coil 200 with a rectangular cross section may have a thickness (in the axial direction) of 0.0016 inches, a width (in the radial direction) of 0.003 inches, a 0.0027-inch pitch, a lateral stiffness of $3\mu$($in^2$-lbs), and a density of 12 g/in. This embodiment may be implemented, for example, in coronary or neuro guidewires.

Figure 4:
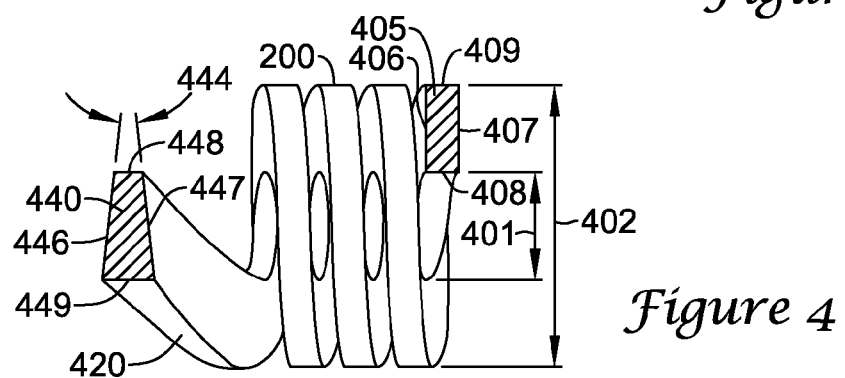
FIG. 4 is a side view illustrating a partially wound coil made from wire having a non-circular cross section.

Referring now to FIG. 4, coil 200 may be wound from wire 420. The cross section 440 of wire 420 may distort or change into cross section 405 when wire 420 is would into coil 200. In order to obtain a particular cross section 405 of the wire forming coil 200, the effect of this distortion may be taken into consideration in selecting the cross section 440 of wire 420. In one embodiment of the present invention, wire 420 may have a circular cross section before being wound, and may have a slightly distorted circular cross section after being wound. As used herein, such a slightly distorted circular cross section is considered to be substantially circular. But in other embodiments, coil 200 may be made so that, when wound, it has a substantially non-circular cross section 405, which may have at least one substantially flat side, for example, side 406. In some embodiments, cross section 405 may also have another substantially flat side 407, which may be substantially parallel to side 406. In some embodiments, cross section 405 may also have substantially flat sides 408, 409, which may be parallel to each other, and may be shorter than sides 406 and 407. Some embodiments may have some combination of substantially flat sides 406, 407, 408, and 409. Cross section 405 may be substantially in the shape of a parallelogram or trapezoid. In the exemplary embodiment illustrated, cross section 405 is substantially in the shape of a rectangle. In embodiments of coil 200 where sides 406 and 407 are large relative to sides 408 and 409 (edge-wound coils or coils having a greater dimension in the radial direction than in the axial direction), the distortion from cross section 440 to cross section 405 will be greatest, but the flexibility of coil 200 will also be greatest, relative to the radial distance [(OD 402)/(ID 401)]/2 available.

Coil 200 may be wound from wire 420, which may have a substantially non-circular cross section 440. Cross section 440 may have two substantially flat opposite non-parallel sides 446 and 447. In some embodiments, sides 446 and 447 may be substantially parallel, and when wound into coil 200, sides 406 and 407 may be out of parallel, with side 408 longer than side 409. In some such embodiments, cross section 440 may have the shape of a rectangle, and cross section 405 may have the shape of a trapezoid. In another embodiment, sides 446 and 447 may be out of parallel by angle 444. Cross section 440 may also have substantially flat sides 448 and 449, which may be shorter than sides 446 and 447, and may form a trapezoid which may be an isosceles trapezoid. In an isosceles trapezoid cross section 440, sides 446 and 447 are of equal length, and sides 448 and 449 are parallel. In some embodiments, side 448, 449, or both, may be curved, and may be convex. Similarly, in some embodiments, side 408, 409, or both, may be curved, and may be convex. In some embodiments, the effect of this curvature may be small or insignificant. But in some embodiments where coil 200 forms the outer surface of the device (e.g., in the embodiments shown in FIGS. 3 and 5), convex curvature of side 409, or a rounding or chamfering of its corners, for example, may improve the lubricity of the medical device against anatomy 101, particularly in locations where extended distal tip 300 is bent around a curve.

In some embodiments, angle 444 and the radius of coil 200 (half of ID 401, half of OD 402, or half of a nominal diameter between 401 and 402) may be selected such that sides 446 and 447 become substantially parallel when wire 420 is wound into coil 200, and sides 446 and 447 become sides 406 and 407 respectively. Thus the amount of keystone shape or angle 444 that may be needed or desirable may depend on the diameter (e.g., ID 401 or OD 402) of the coil 200 to be wound. The smaller the coil 200 diameter, the more keystone shape or angle 444 may be needed to compensate for the deformation in the wire 420 as it bends into coil 200. Other variables may affect the angle 444, including the thickness (in the axial direction) of cross section 405 (e.g., the length of side 408 or 409). The shape of cross section 440 may be determined by calculation, empirically, or a combination thereof, to obtain a desired cross section 405. Cross section 440 may be formed, for example, by drawing, rolling, grinding, or machining wire 420, or a combination thereof. Once the wire is formed with cross section 440, the wire may be wound into coil 200 with cross section 405. In various embodiments of the present invention, coil 200 may be wound onto a medical device such as guidewire 100, or may be installed onto the medical device in a separate step.

FIG. 2 also illustrates an exemplary embodiment of the present invention having a proximal chamfer 231 in proximal end 139 of tubular member 130. Proximal chamfer 231 may be flat (e.g., a conic section) or curved (e.g., a radiused corner). Proximal chamfer 231 may be beneficial, for example, in embodiments wherein core wire 150 is gradually tapered at joint 140, or wherein proximal section 159 of core wire 150 has a smaller OD than that of proximal end 139 of tubular member 130. For example, chamfer 231 may help provide a smooth transition in diameter from that of proximal section 159 of core wire 150 to proximal end 139 of tubular member 130. This may facilitate removal of guidewire 100, reduce trauma to anatomy during removal, or both. Proximal chamfer 231 may also facilitate a more gradual change in bending stiffness, reduce stress concentration, provide more surface area for bonding, or a combination of these benefits. Proximal chamfer 231 may be implemented, for example, in neuro guidewires.

FIG. 2 also illustrates an exemplary embodiment of the present invention having a relatively soft material 261 between at least part of distal section 158 of core wire 150 and tubular member 130. In addition, or in the alternative, material 261 may fill or partially fill at least some of slots 135. Material 261 may comprise urethane, an epoxy, an adhesive, or a polymer, for example. Material 261 may increase the stiffness of guidewire 100. Thus, more slots 135 may be required to obtain a desired bending stiffness. The greater number of slots 135, with less angle of bending per slot 135, may result in a greater fatigue life of tubular member 130. Increasing stiffness with material 261 rather than by using a larger diameter distal section 158 of core wire 150 may help to avoid plastic deformation or fatigue of section 158 of core wire 150 for a given radius of bending, for example in particularly tortuous vasculature 105. In addition, in embodiments where material 261 fills at least some of slots 135, material 261 may provide a more constant outside diameter reducing friction between at least that portion of guidewire 100 and anatomy 101.

FIGS. 2 and 3 also illustrate that section 158 of core wire 150 may extend distally from joint 140 to distal tip 257 at distal end 138 of tubular member 130 or to distal tip 137. Distal tip 257 of section 158 of core wire 150 may attach to tubular member 130. In some embodiments, this may be accomplished by attaching distal end 138 of tubular member 130 and distal tip 257 of core wire 150 both to distal tip 137. As used herein, core wire 150 is said to be attached to tubular member 130 if core wire 150 is attached directly to tubular member 130 (e.g., with solder or adhesive) or if core wire 150 is attached (e.g., with solder or adhesive 347) to a coil (e.g., 1141 or 200), busing (e.g., 757) or tip 137, for example, and tubular member 130 is also attached (e.g., with solder or adhesive 347) to this same coil, bushing, or tip 130 at substantially the same location along the longitudinal axis of the device.

Figure 6:
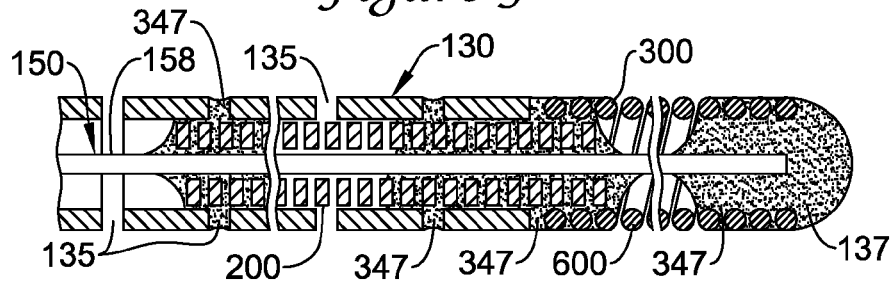
FIG. 6 is a cross-sectional side view illustrating the distal end of an embodiment of a medical device in accordance with the present invention having an extended coil tip and an internal coil.

In embodiments having an extended coil tip 300, the distal end of coil 200 and the distal tip 257 of core wire 150 may be attached to each other directly or via tip 137. An exemplary embodiment is illustrated in FIG. 3. In some embodiments, distal end 138 of tubular member 130 may be attached to core wire 150, for example, through a coil, solder, adhesive, or a combination thereof. An exemplary embodiment where in core wire 150 is attached to distal end 138 of tubular member 130 (via coil 200 and solder or adhesive 337) is illustrated in FIG. 6. In the embodiment illustrated, distal tip 257 of core wire 150 is also attached to distal tip 137 and the distal end of extended coil tip 300. But extended coil tip 300 may not be very stiff in torsion. Thus, if tip 137 is rotated relative to tubular member 130, for example, and distal section 158 of core wire 150 is completely attached at distal end 138 of tubular member 130, and at distal tip 137, then section 158 of core wire 150 may be damaged by exceeding its yield stress or recoverable strain in torsion.

To solve this potential problem, the connection of core wire 150 to distal end 138 of tubular member 130, to coil 200, or to tip 137 may be configured in some embodiments to protect core wire 150 inside the extended coil tip 300 from exposure to excessive toque. For instance, in some embodiments, core wire 150 may not be bonded to distal end 138 of tubular member 130, or to coil 200 at that location. An example of such an embodiments is illustrated in FIG. 3. A bushing 338 may be used at distal end 138 of tubular member 130 to isolate section 158 of core wire 150 from the adhesive or solder 347 used to attach distal end 138 of tubular member 130 to coil 200 of extended coil tip 300. Bushing 338 may also provide more bending strength, tensile strength, torsional strength, or a combination thereof in the joint, and may center guidewire 150. Bushing 338 may be, for example, a section of tube or coil.

Figure 5:
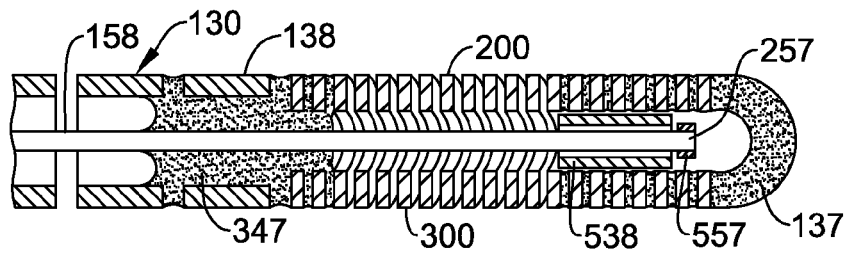
FIG. 5 is a cross-sectional side view illustrating the distal end of an embodiment of a medical device in accordance with the present invention having an extended coil tip and a core wire configured to be free to rotate within the tip of the device.

In another exemplary embodiment illustrated in FIG. 5, distal tip 257 of core wire 150 may be axially but not torsionally constrained at distal tip 137 of extended coil tip 300. In the embodiment illustrated, bushing 538 is attached to the distal end of extended coil tip 300 or to distal tip 137 of guidewire 100. Distal section 158 passes through bushing 538 and its distal tip 257 is attached to bushing 557. Bushings 538 and 557 may be sections of tube or coils, for example. Thus, distal tip 257 of core wire 150 is free to rotate within extended coil tip 300, but when distal section 158 of core wire 150 is loaded in tension, bushing 557 will push on bushing 538, allowing section 158 of core wire 150 to pull distal tip 137.

FIG. 6 illustrates another exemplary embodiment of the present invention having an extended coil tip 300, this embodiment having coil 600 with a substantially circular cross section. Coil 600 may be made of a substantially radiopaque material. As illustrated, such an embodiment may also comprise coil 200, which may be an edge wound coil, and may have a substantially rectangular cross section as shown. Coil 200 in this embodiment may be made of a substantially radiopaque material and may provide additional radiopacity to that of coil 600. Coil 200 may also contribute to the joint between tubular member 130, coil 600, core wire 150, or some combination of these components. Solder or adhesive 347 may bond to tubular member 130, coil 200, coil 600, core wire 150, or some combination of these. As an example, in the embodiment illustrated, solder or adhesive 347 is located at both ends of coil 200. Solder or adhesive 347 may also be used to bond coil 600, distal end 137, core wire 150, coil 200, or some combination of these components, at distal tip 137, distal end 138, or distal tip 257. In other embodiments, a second tubular member (slotted or otherwise) may be used in lieu of coil 200, coil 600, or both.

Figure 7:
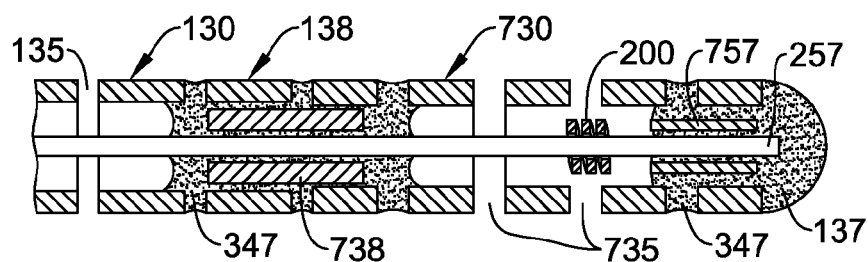
FIG. 7 is a cross-sectional side view illustrating the distal end of an embodiment of a medical device in accordance with the present invention having two tubular members arranged in line.

Another exemplary embodiment of the present invention that may provide adequate radiopacity is illustrated in FIG. 7 and involves a second tubular member 730 of a substantially radiopaque material, which may have good spring characteristics, such as platinum/tungsten, platinum/iridium, or platinum/iridium/rhodium. Tubular member 730 may have a plurality of slots 735 configured to make tubular member 730 more flexible in bending. For example, slots 735 may be like an embodiment of slots 135 described herein for tubular member 130. Tubular member 730 may be located at the distal section 158 of core wire 150, and may extend to or near distal tip 257. This embodiment may allow better torque transmission to tip 137 than would be provided by an extended coil tip 300, and may also provide high radiopacity, when compared with other embodiments such as the embodiment illustrated in FIG. 2. In some embodiments, a coil 200 may be located within tubular member 730 which may provide additional stiffness, radiopacity, or both.

The length of tubular member 730 may be, for example, within the range from 0.5 cm to 5 cm. In various embodiments, the wall thickness of the radiopaque tubular member 730 may be substantially the same or different than that of tubular member 130. Coils or bushings 738, 757, or both may be used at the ends of tubular member 730 to center core wire 150 in the joint, to facilitate attachment, or both. Solder or adhesive 347 may be used to attach distal end 138 of tubular member 130, core wire 150, or both, to tubular member 730. Solder or adhesive 347 may also be used in some embodiments to attach tubular member 730 to distal tip 137 of guidewire 100, distal tip 257 of core wire 150, or both.

Figure 8:
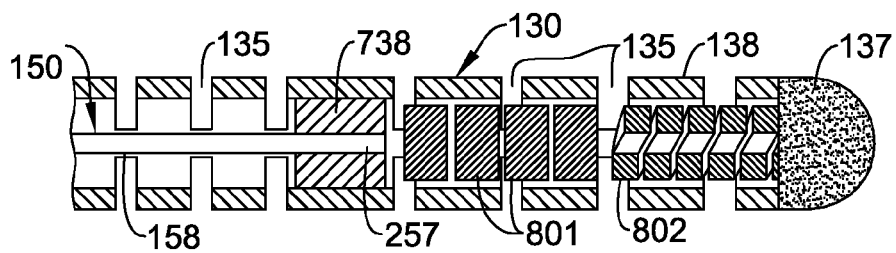
FIG. 8 is a cross-sectional side view illustrating the distal end of an embodiment of a medical device in accordance with the present invention having a core wire that terminates proximal to the distal end of the device, and substantially radiopaque material inside the distal end of a tubular member.

Still another exemplary embodiment of the present invention that may provide adequate radiopacity is illustrated in FIG. 8. In this exemplary embodiment, core wire 150 is terminated at distal tip 257 proximal to distal end 138 of the micromachined tubular member 130, or proximal to distal tip 137. Thus the full lumen diameter of tubular member 130 distal to distal tip 257 of core wire 150, or a greater part of this diameter, may then be available to be filled with radiopaque material. This substantially radiopaque material may be, as examples, in the form of disks 801, spheres, coils 802, or micromachined or slotted wire. Distal tip 257 of core wire 150 may attach to tubular member 130, for example, through coil or bushing 738, solder, adhesive, or a combination thereof.

Various embodiments of the present invention include medical devices, such as guidewire 100, with a tip or distal end 138 with a relatively high flexibility, a relatively high tensile strength, or both, as well as methods for constructing such devices. Specifically, in many embodiments of the present invention, it may be desirable that the tip or distal end 138 of guidewire 100, for example, be of low stiffness to prevent perforation or dissection, for example, of anatomy 101 or vasculature 105. This may be achieved by grinding distal section 158 of core wire 150 to a small diameter or by creating a flat or ribbon shaped wire at the distal end. In guidewire 100, tubular member 130 may carry the torsion load (e.g., during removal of guidewire 100), at least in the section distal to joint 140, and section 158 of core wire 150 may only be required to carry tensile loads in that section. It may also be desirable to allow tubular member 130 (rather than section 158 of core wire 150) to provide most of the desired bending stiffness in the section distal to joint 140 because this may maximize the torque carrying ability of tubular member 130.

Figure 9:
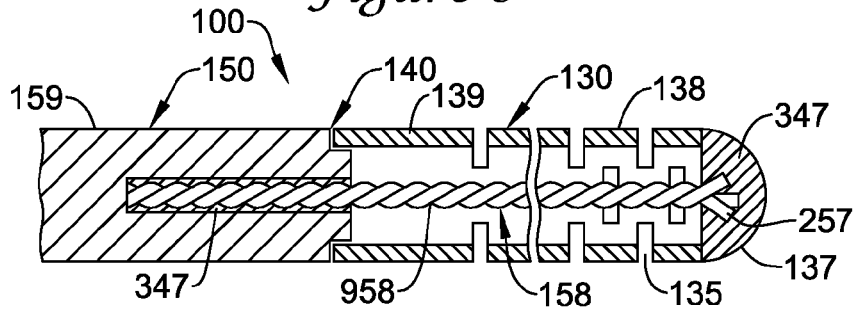
FIG. 9 is a cross-sectional side view illustrating the distal end of an embodiment of a medical device in accordance with the present invention having a core wire with a distal section comprised of a plurality of strands of material twisted together.

Thus, referring to FIG. 9, it may be advantageous to utilize a section 158 of core wire 150 for guidewire 100 that maximizes its tensile strength and minimizes its bending stiffness. This may be achieved by making section 158 of core wire 150 from a plurality of smaller wires 958 which may be braided or twisted together to achieve the same tensile strength as one much larger wire. In other embodiments, strands or wires 958 may be parallel. Another embodiment is to utilize a polymer filament with high tensile strength but low stiffness such as polyethylene (for example, SPECTRA fiber from ALLIED SIGNAL) or polypropylene, for section 158 of guidewire 150. The polymer core wire may also be stranded in some embodiments, for example, for additional bending flexibility, and may be twisted, braided, or parallel.

In embodiments of the present invention wherein section 158 of core wire 150 has a plurality of metal strands 958, for example braided or twisted stainless steel cable or wire rope, distal section 158 may be attached to proximal section 159 of core wire 150 with solder or adhesive 347 as shown in FIG. 9. Distal section 158 may also be attached to distal tip 137, for example, with solder or adhesive 347. In various embodiments, distal section 137 may be formed from a ball or hemisphere of solder or adhesive 347 surrounding the distal tip 257 of distal section 158. Embodiments of the present invention wherein section 158 comprises one or more polymer filaments may be similar, except that an adhesive may be used rather than solder. For example, an epoxy may be used. The bond between section 158 and 159 of core wire 150 may be tensile tested for quality assurance purposes.

FIG. 10 illustrates another embodiment of the present invention having a relatively high bending flexibility in the tip, but only in one direction of bending. This exemplary embodiment has a flattened core wire 150 at the distal tip 257 of distal section 158. Specifically, the distal end 257 of core wire 150 may be flattened to achieve a more flexible distal tip 1057. This may be done on embodiments with or without an extended coil distal tip 300 (e.g., coil 200 illustrated in FIG. 3). As used herein, a tip or cross section is considered to be flattened if it has one dimension (perpendicular to the axis) that is at least twice the other dimension (perpendicular to both the axis and to the first dimension). An example of a flattened tip 1057 would be 1 cm long and flattened from a 0.002-inch round core wire (section 158) to 0.001-inch× 0.003-inch. In various embodiments, the range of flattened length may be from 0.5 to 5 cm, for example. In some embodiments, a portion of distal section 158 other than distal tip 257 may be flattened. Flattening a section of core wire 150, for example, from a substantially round cross section, may provide greater flexibility in one plane, while providing less flexibility in a perpendicular plane, both planes passing through the axis of guidewire 100. Distal tip 1057 may be flattened by rolling or forging, for example.

In embodiments having a flattened distal tip 1057, one or more pieces of substantially radiopaque material 1001 may be located inside tubular member 130, for example, at distal end 138. Material 1001 may be in the form of one or more pieces which may have a substantially semicircular cross section, be slotted disks, or be in the shape of a coil or a coil with a notch formed in the ID, for example. Material 1001 may be located on opposite sides of the substantially flat cross section of the distal section 158 or distal tip 257 of core wire 150.

The present invention also includes medical devices having a number of embodiments of joint 140, for example, medical devices such as guidewire 100 having tubular member 130 and core wire 150. Various embodiments of joint 140 are illustrated, as examples, in FIGS. 11-15. The present invention also includes various methods of fabricating these devices, which are described herein. The construction of the proximal joint 140 between the micromachined tube or tubular member 130 and the core wire 150 in various embodiments of a guidewire 100 with these components may be a factor in the performance of the guidewire 100. Referring to FIG. 1, joint 140 may, in various exemplary embodiments, transfer the torque from the proximal section 159 of the core wire 150 to the proximal end 139 of tubular member 130. In many embodiments, it may be desirable that joint 140 be sufficiently short, flexible or both, so as to not adversely affect the bending stiffness profile or characteristics of guidewire 100. Joint 140 may, in an exemplary embodiment of the present invention, also be strong and rugged enough to undergo the simultaneous or separate application of torsion, tension, and bending that may occur during use.

Referring now to FIGS. 11-15, common to various embodiments of joint 140 may be the use of a coil or section of coil 1141 circumscribing core wire 150 and at least partially inside tubular member 130 to strengthen joint 140 between core wire 150 and tubular member 130. Section or coil 1141 may be located at least part way inside proximal end 139 of tubular member 130 as shown, and may be stretched, for example, with a pitch of from 1.5 to 5 times the diameter of the wire from which coil 1141 is made. Coil 1141 may be attached to core wire 150 and tubular member 130 with solder 1147, adhesive 1148, or both. In some embodiments, coil 1141 may be attached to core wire 150 with solder 1147, and then attached to tubular member 130 with adhesive 1148. Such a joint 140 may be stronger than adhesive 1148 alone because adhesive 1148 may flow in and around coil 1141 and in some embodiments also cuts or slots 135 in tubular member 130 and create a mechanically interlocked structure that may have strength even in the event of a complete lack of microscopic adhesion of adhesive 1148 to core wire 150, tubular member 130, or both. Coil 1141 may be made from a metal, for example, stainless steel, or in some embodiments, a substantially radiopaque-material such as platinum or tungsten.

Various embodiments of the present invention may have one or more intermediate bonds between core wire 150 and tubular member 130. In such embodiments of the present invention, tubular member 130 may be bonded (e.g., with adhesive 1148) directly to core wire 150, or to a coil, which may be similar to coil 1141. Such bonds may be, for example, at one or more points intermediate proximal end 139 and distal end 138 of tubular member 130. These bonds may transfer torsional or axial forces or both between the two structural members (tubular member 130 and core wire 150). This embodiment may be implemented, for example, in neuro guidewires.

In exemplary embodiment 1240 of the present invention illustrated in FIG. 12, joint 140 may be constructed at least partially within a tapered portion 1253 of core wire 150. A mesial coil 1243, a proximal coil 345, or both may also be soldered to core wire 150, for example, in the locations shown. In alternate embodiments, coil 1141 may be part of mesial coil 1243 (but may have a different pitch) or may be a separate coil. Mesial coil 1243 may be a marker coil, such as coil 200 illustrated in FIG. 3. It may be advantageous in some embodiments to terminate a marker coil (e.g., 200) and begin another coil (e.g., mesial coil 1141 or 1243) of another material. For instance, one material may be less expensive than the other, but may be suitable for use in part of the coil. For example, a platinum marker coil 200 could be terminated and a stainless steel coil 1141 could continue in its place. In addition, or in the alternative to a reduction in material cost, using another material may provide more compressive strength or stiffness to a medical device such as guidewire 100. Such an embodiment may be implemented, for example, in a coronary wire.

In order to provide a smoother diameter transition, particularly for embodiments of guidewire 100 that have a relatively short micromachined tubular member 130, a proximal coil 345 may be used. Proximal coil 345 is shown, for example, in FIGS. 3 and 12-15. Proximal coil 345 may have an outside coil diameter that may be about the same as that of proximal section 159 of core wire 150, slotted tubular member 130, or both. Proximal coil 345 may be made, for instance, of stainless steel or other metals. In various exemplary embodiments, the length of proximal coil 345 may range from 1 to 30 cm. The termination of proximal coil 345 on its proximal end may be, for example, at the point where the inner diameter of proximal coil 345 matches the outer diameter of core wire 150. This embodiment of the present invention may be implemented, for instance, in a coronary wire.

In embodiments having solder 1147 and adhesive 1148, the quantity of solder 1147 in the spaced or stretched coil 1141 (or section 1141 of the mesial coil 1243) may be controlled so that coil 1141 may be soldered to core wire 150 but solder 1147 does not completely fill the spaces between the loops of coil 1141. Tubular member 130 may then be slid over coil 1141, mesial coil 1243, or both, and may butt up against proximal coil 345. Adhesive or glue 1148 may then be wicked into the space between the core wire and the tube in the location shown, attaching core wire 130 at its proximal end 139 to coil 1141 and core wire 150. Adhesive 1148 may form a mechanical interlock against coil 1141, within slots 135, or both.

Referring to FIG. 13, which illustrates another exemplary embodiment of joint 140, joint embodiment 1340 may be constructed over a feature in core wire 150 or an abrupt change in cross-sectional dimension or diameter, such as a ridged section 1351 of core wire 150, which may be located between proximal section 159 and distal section 158. Ridge or ridged section 1351 may be a feature in core wire 150 configured to facilitate mechanical interlock of solder or adhesive 347, for example, used for joint 140. Other such features or abrupt changes in cross-sectional dimension or diameter may include steps, ridges of other shapes (e.g., shorter in axial length), grooves, slots, changes in cross section (e.g., round to polygonal), or a combination of such features.

Ridged section 1351 may be formed, for example, by grinding down the remainder of core wire 150, or by installing a coil or sleeve on core wire 150, which may be soldered, welded, bonded, shrunk fit, cast, or crimped in place. A coil 1141, which may be part of a mesial coil 1143, may be soldered to core wire 150 just distal to the ridge 1351 as shown. Again, the quantity of solder 1147 in the spaced coil section 1141 of the mesial coil 1143 may be controlled so that the coil 1141 may be soldered to the wire but, in some embodiments, solder 1147 may not fill the spaces between the loops of coil 1141. In some embodiments, a proximal coil 345 may be soldered to the proximal section 159 of core wire 150, to ridge 1351, or both. Tubular member 130 may then be installed over core wire 150, for instance, to the point where proximal end 139 butts up to proximal coil 345. Adhesive or glue 1148 may be wicked into the space between tubular member 130 and core wire 150 in the location shown.

The embodiment of joint 140 illustrated in FIG. 11 may have the advantage of not requiring a specific feature or abrupt change in cross-sectional dimension or diameter like a step, ridge, or shelf on the ground section of core wire 150. But this embodiment may have the disadvantage of having a point at or just proximal to proximal end 139 of tubular member 130 where the bending stiffness of the assembled guidewire 100 may be lower than the adjacent portions of guidewire 100. In some applications, this may lead to fatigue and failure at joint 140 in use. Joint embodiment 1340, illustrated in FIG. 13, may have a short extra stiff segment at the proximal end 139 of tubular member 130 at ridge 1351 in core wire 150. This embodiment 1340, however, may yield a more rugged joint 140 when exposed to repeated bending stress. In some embodiments, the diameter of ridge 1351, other factors, or a combination thereof, may be selected to obtain a relatively continuous bending stiffness in the area of joint 140.

Figure 14:
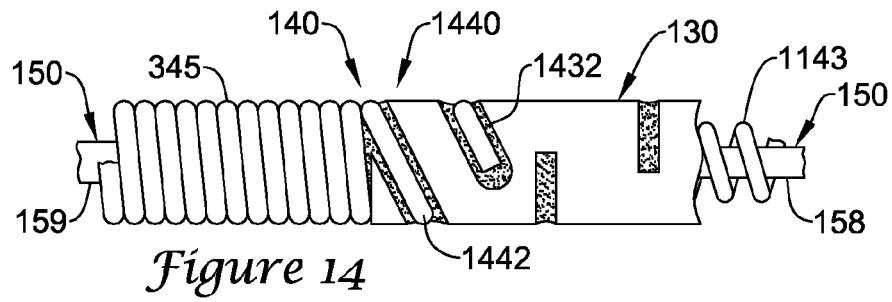
FIG. 14 is a side view illustrating an embodiment of a mesial joint in accordance with the present invention a coil partially located within a helical cutout in a tubular member.

FIG. 14 illustrates still another exemplary embodiment of the present invention, joint 140 embodiment 1440, which, like the embodiment illustrated in FIG. 11, may be constructed on a tapered portion of core wire 150. Mesial coil 1143 and proximal coil 345 may be attached to core wire 150 in the locations shown in FIGS. 11 and 14, for example, with adhesive 1148, solder 1147, or both. In embodiments having both solder 1147 and adhesive 1148, the quantity of solder 1147 in the spaced coil section 1141 of mesial coil 1143 may be controlled so that solder 1147 does not fill the spaces between the loops of coil 1141. In embodiment 1440, proximal coil 345 may have a short spaced-apart region 1442 at it's distal end that screws into a matching helical cutout 1432 in tubular member 130. Solder 1147 or adhesive or glue 1148 may be wicked into the space between tubular member 130 and core wire 150 in the location shown. Thus, joint 140 embodiment 1440 may interlock proximal coil 345 with tubular member 130, which may provide a stronger connection than some alternatives.

Figure 15:
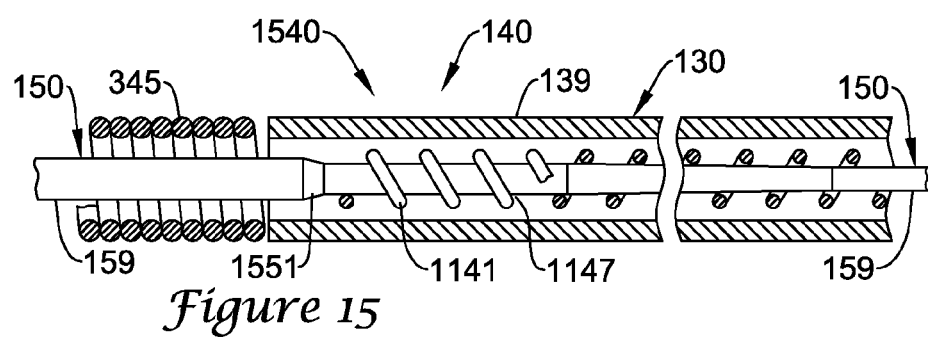
FIG. 15 is a partially cross-sectional side view illustrating an embodiment of a mesial joint in accordance with the present invention having two coils, one inside a tubular member, and the other abutting the tubular member.

FIG. 15 illustrates yet another exemplary embodiment of the present invention, joint 140 embodiment 1540, which may be constructed at an abrupt change in cross-sectional dimension such as step 1551 in the diameter of core wire 150. Step 1551 may be a feature in core wire 150 configured to facilitate mechanical interlock of solder or adhesive 347, for example, used for joint 140. In various embodiments, step 1551 may be a relatively steep taper as shown, or may be a square step in diameter, i.e., with a surface perpendicular to the axis of core wire 150. Radiused inside corners (for example, such as those shown for ridge 1351 in FIG. 13) may reduce stress concentration. Coil 1141 or section 1141 of mesial coil 1143 may be attached to core wire 150 at or just distal to step 1551 as shown. As in other embodiments, solder 1147, adhesive 1148, or both, may be used to attach coil or section 1141 to core wire 150. In some embodiments, the end of proximal coil 345 may be attached proximal to step 1551 as shown. Tubular member 130 may then be installed on core wire 150 to the point where it butts up to proximal coil 345. Solder 1147 or adhesive or glue 1148 may be wicked into the space between tubular member 130 and core wire 150 in the location shown. Joint 140 embodiment 1540 may be similar to joint 140 embodiment 1340 in that it may reduce or eliminate a potential weak spot at proximal end 139 of tubular member 130. Embodiment 1540 may be less costly to produce because of the step 1551 rather than a ridge 1351, but some embodiments 1540 may be not be quite as rugged as some embodiments of 1351, for example, in embodiments having a radial gap between tubular member 130 and core wire 150 at the extreme proximal end of tubular member 130.

Joint 140 with step 1551 may be useful, for example, on guidewires that have a short length of tubular member 130, for instance, a coronary wire with a 5 cm tubular member 130. In such an exemplary embodiment, core wire 150 may be substantially smaller than the inner diameter of tubular member 130. Step 1551 in core wire 150 may allow joint 140 at proximal end 139 of tubular member 130 to have sufficient strength in bending. Step 1551 in core wire 150 may, as examples, either be ground in place on core wire 150, or a distal tube may be slid over proximal section 159 of core wire 150 and soldered or bonded, for instance, to core wire 150 as a separate operation.

Figure 16:
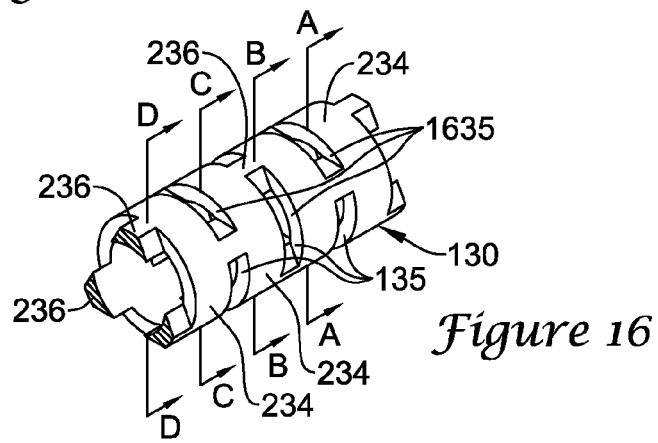
FIG. 16 is an isometric view of a section of one embodiment of a tubular member in accordance with the present invention having slots formed therein in groups of three, wherein the slots are equal in size and equally spaced around the axis of the tubular member.
Figures 16A, 16B:
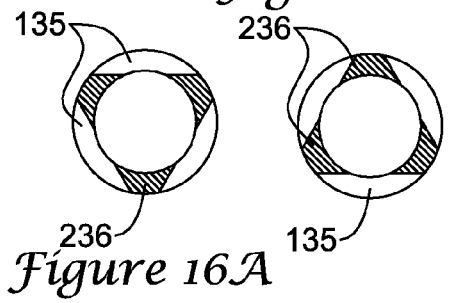
FIGS. 16A through 16D are cross-sectional end views showing cross sections of the slots and segments there between of the embodiment of the tubular member illustrated in FIG. 16.
Figures 16C, 16D:
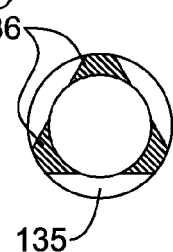

The present invention also includes various embodiments of arrangements and configurations of features making it more flexible in bending, for example, slots 135. As mentioned with reference to FIG. 1, tubular member 130 may have a plurality of slots 135 formed or cut into tubular member 130 to make it more flexible in bending. Referring to FIG. 2, slots 135 may be formed part way through tubular member 130, leaving axial beams or segments 236 joining rings 234. Various embodiments of tubular member 130 are illustrated in FIGS. 16-19, with various configurations and arrangements of slots 135, rings 234, and segments 236. Specifically, slots 135 may be formed in groups of two, three, or more slots 135, which may be located at substantially the same location along the axis of tubular member 130, and may be substantially perpendicular to the axis. FIG. 2 illustrates an exemplary embodiment having groups 235 of two slots 135 each, and FIG. 16 illustrates an exemplary embodiment having groups 1635 of three slots 135 each. A ring 234 is formed between any two adjacent groups (e.g., 235 or 1635) of slots 135, and adjacent rings 234 are attached by a number of segments 236 equal to the number of slots 135 in the group 235. With groups 235 of two slots 135, bending of tubular member 130 may result from distortion of segments 236, rings 234, or both. With groups 235 of three or more slots, bending of tubular member 130 results more from distortion of rings 234. Thus, fatigue is less likely occur at segments 236 in embodiments having three or more slots 135 per group 235.

Adjacent groups 235 or 1635 of slots 135 may be rotated by an angle relative to each other (i.e., from the adjacent or previous group 235 or 1635) about the axis of tubular member 130 as illustrated in FIG. 3 and FIG. 16. Adjacent groups 235 consisting of two slots 135 may be rotated by and angle of about 90 degrees, for example, and adjacent groups 1635 consisting of three slots may be rotated by an angle of about 60 degrees. Thus, segments 236 may approximately line up in the axial direction with the midpoints of the adjacent slots 135. In general, this angle of rotation may be about 180 degrees divided by the number of slots 135 in the group (e.g., group 235 or 1635).

In some embodiments, the angle of rotation may be slightly more or slightly less than the angle given by this formula. Thus, segments 236 may be a slight angle from lining up with the midpoint of slots 135 in adjacent groups. Thus, slots 236 may form a helical pattern along tubular member 130. This slight angle may be, for example, 1 to 20 degrees for groups 235 of two slots 135 each, and may be the same or less for groups having more than two slots 135. In general, the angle of rotation may be 180 degrees plus or minus no more than 40 degrees, that quantity divided by the number of slots 135 in the group (e.g., group 235 or 1635). In other words, the angle of rotation may be within the range of 140 to 220 degrees divided by the number of slots 135 in the group (e.g., group 235 or 1635). In other embodiments, the angle of rotation may be 180 degrees plus or minus an angle between 1 and 25 degrees, that quantity divided by the number of slots 135 in the group (e.g., group 235 or 1635). In other embodiments, the angle of rotation may be 180 degrees plus or minus no more than 5 degrees, that quantity divided by the number of slots 135 in the group (e.g., group 235 or 1635). In still another embodiment, the angle of rotation may be 180 degrees divided by the number of slots in the group, plus or minus no more than 10 degrees or 1 to 10 degrees.

Figure 17:
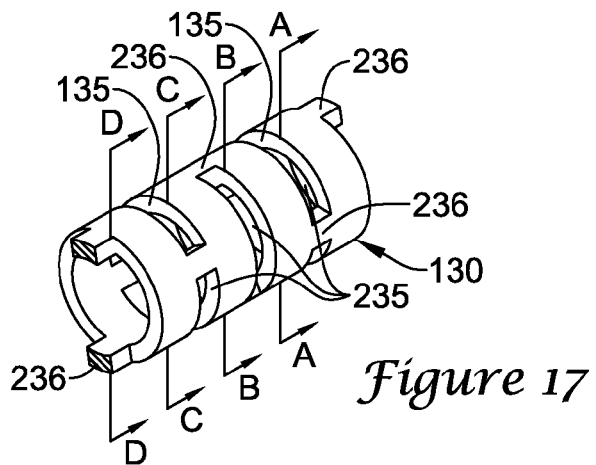
FIG. 17 is an isometric view of a section of one embodiment of a tubular member in accordance with the present invention having equal size slots formed therein in groups of two, wherein adjacent groups are rotated 85 degrees around the axis of the tubular member.
Figure 17A:
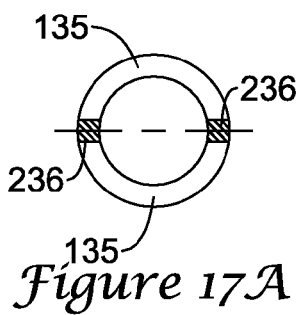
FIGS. 17A through 17D are cross-sectional end views showing cross sections of the slots and segments there between of the embodiment of the tubular member illustrated in FIG. 17 showing the angle of rotation between adjacent groups of slots and segments.
Figure 17B:
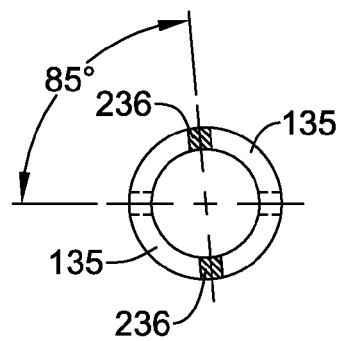
Figure 17C:
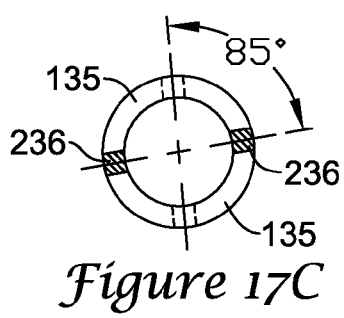
Figure 17D:
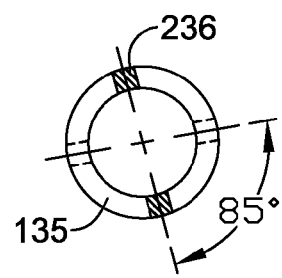

FIG. 17 illustrates an exemplary embodiment wherein groups 235 of two slots 135 each are rotated by an angle of approximately 85 degrees from the adjacent group 235. Thus, group 235 at section B is rotated approximately 85 degrees from group 235 at section A, group 235 at section C is rotated approximately 85 degrees from group 235 at section B, and group 235 at section D is rotated approximately 85 degrees from group 235 at section C. Thus, in this embodiment, segments 236 form a helical pattern along tubular member 130. Slots 135 may be formed by cutting or grinding, for example, with a semiconductor dicing blade. For instance, each slot 135 in a group 235 may be cut in turn by rotating tubular member 130. Then tubular member 130 may be advanced axially, rotated the desired amount, and the axially adjacent group 235 of slots 135 may be cut. In the embodiment illustrated in FIG. 17, this desired amount would be 85 degrees. Rotating by 95 degrees would provide the same result, except that the helical pattern would be in the opposite direction.

In some embodiments of the present invention, it may be advantageous to form slots 135 of one or more of the configurations and arrangements described herein in a solid member or wire rather than in a tubular member (e.g., tubular member 130). For example, groups 235 of two slots 135 each may be formed in a solid circular cylinder or wire, which may be formed from nitinol or stainless steel, for example. In some embodiments, different materials may be joined, for example, a stainless steel proximal section and a nitinol distal section, both of which or just the distal section being slotted. Tapering or changes in diameter may also facilitate a lower bending stiffness at the distal end. In comparison with a slotted tubular member 130, for example, a slotted solid member may have greater tensile strength due to the center portion.

As an exemplary embodiment, slots 135 may be formed in part or all of proximal section 159 or distal section 158 of core wire 150 of the exemplary embodiment's described or illustrated herein. In one embodiment, such a slotted wire may form a guidewire, which may have a coil (e.g., an external radiopaque coil 200), tubular member (e.g., 130), coating, or a combination of these. Some embodiments may be encapsulated with a radiopaque polymer compound, for example. In some embodiments, there may be a slotted wire in a slotted tubular member 130, in a radiopaque slotted tubular member 730 (shown in FIG. 7), or both. In another example, such a slotted solid member or wire may be formed of a substantially radiopaque material and used as a marker, for example, in lieu of disks 801 or coil 802 in the exemplary embodiment illustrated in FIG. 8.

In some embodiments, slots 135 may be substantially equally spaced around the axis, as shown, for example, in FIGS. 2, 3, and 16. In such embodiments, each slot 135 in a group 235 may be substantially the same size (e.g., width and depth). However, in some embodiments, slots 135 may be spaced unequally around the axis, may be of unequal sizes, or both. As an example, as illustrated in FIG. 18A, slot 1835a may be substantially deeper than slot 1835b, thus resulting in segments 1836 being offset from the center of tubular member 130. In the embodiment illustrated in FIG. 18, every other (every second) group 236 has unequally sized slots 135. In the embodiment illustrated in FIG. 19, every group 235 shown has unequally sized slots 135. Further, in the embodiment illustrated in FIG. 18, all of the groups of unequal depth slots 1835a and 1835b are formed so that segments 1836 are offset in substantially the same direction relative to the axis of tubular member 130. In contrast, the embodiment illustrated in FIG. 19 shows that unequal depth slots 1835a and 1835b may be formed so that segments 1836 are offset in different directions relative to the axis of tubular member 130. In some embodiments, for example, a plurality of directions equally spaced around the axis may have equal numbers of deeper slots 1835a. Such embodiments may have essentially equal bending characteristics around the axis. In some embodiments of the present invention, slots 1836b may be omitted, resulting in one slot 1835a per group 235.

Figure 18:
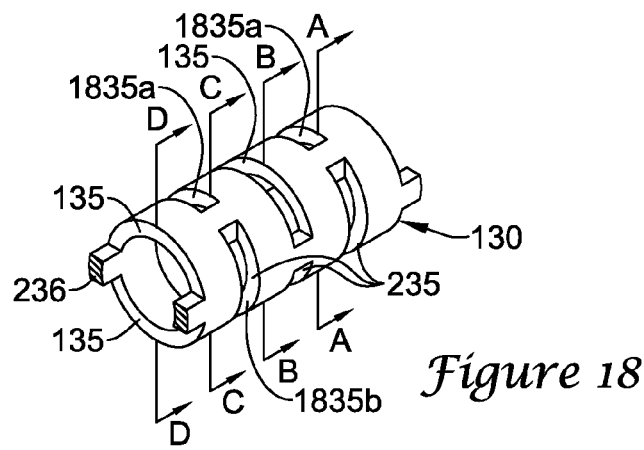
FIG. 18 is an isometric view of a section of one embodiment of a tubular member in accordance with the present invention having slots formed therein in groups of two, wherein some groups of slots contain slots of unequal depth.
Figure 18A:
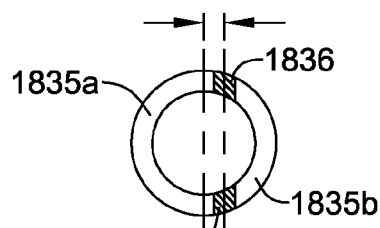
FIGS. 18A through 18D are cross-sectional end views showing cross sections of the slots and segments there between of the embodiment of the tubular member illustrated in FIG. 18.
Figure 18B:
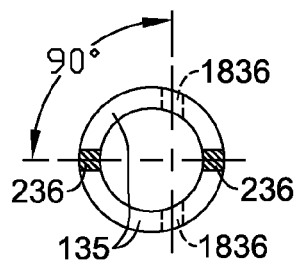
Figure 18C:
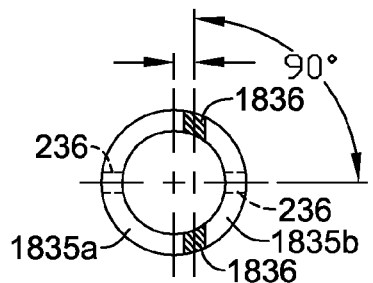
Figure 18D:
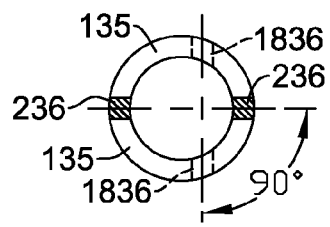
Figure 19:
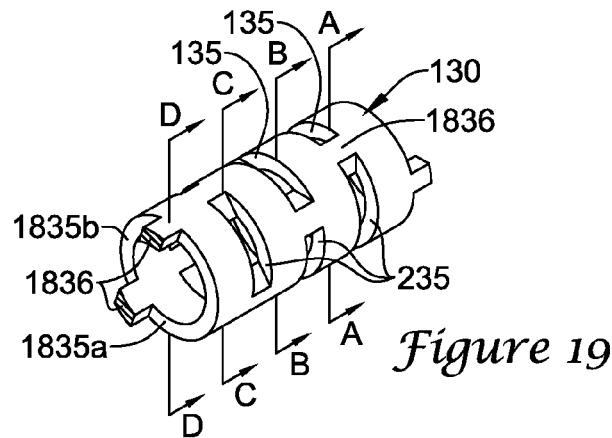
FIG. 19 is an isometric view of a section of one embodiment of a tubular member in accordance with the present invention having slots formed therein in groups of two, wherein all of the groups contain slots of unequal depth.
Figure 19A:
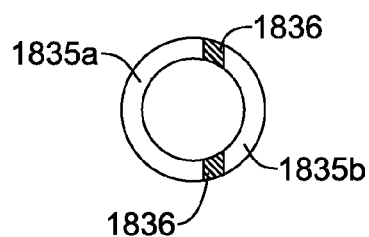
FIGS. 19A through 19D are cross-sectional end views showing cross sections of the slots and segments there between of the embodiment of the tubular member illustrated in FIG. 19.
Figure 19B:
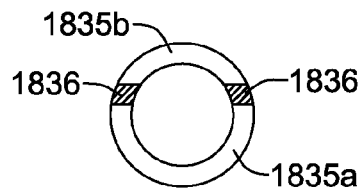
Figure 19C:
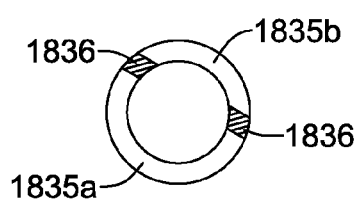
Figure 19D:
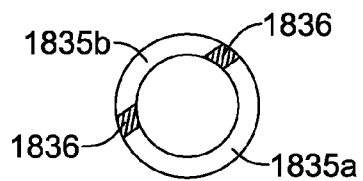
Figure 20:
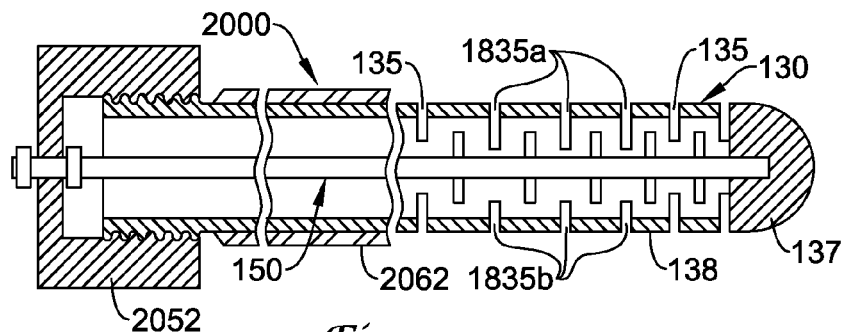
FIG. 20 is a partially cross-sectional side view illustrating an embodiment of a steerable medical device in accordance with the present invention having a tubular member with slots formed and arranged like the embodiment shown in FIG. 18.
Figure 20A:
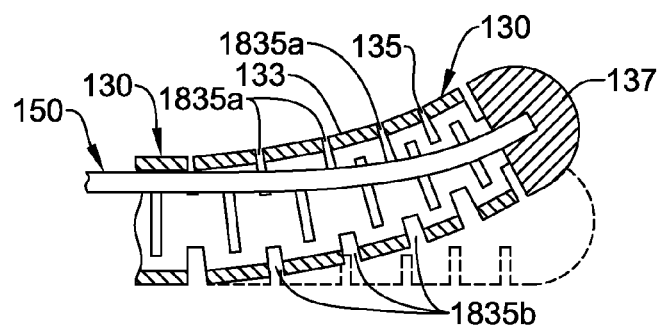
FIG. 20A is a partially cross-sectional side view illustrating the tip of the embodiment of a steerable medical device shown in FIG. 20 adjusted into a bend.
Figure 21:
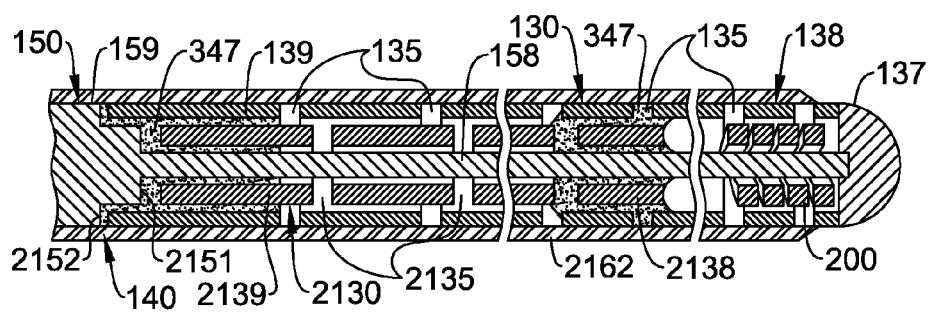
FIG. 21 is a cross-sectional side view illustrating the distal end of an embodiment of a medical device in accordance with the present invention having three tubular members arranged coaxially.
Figure 22:
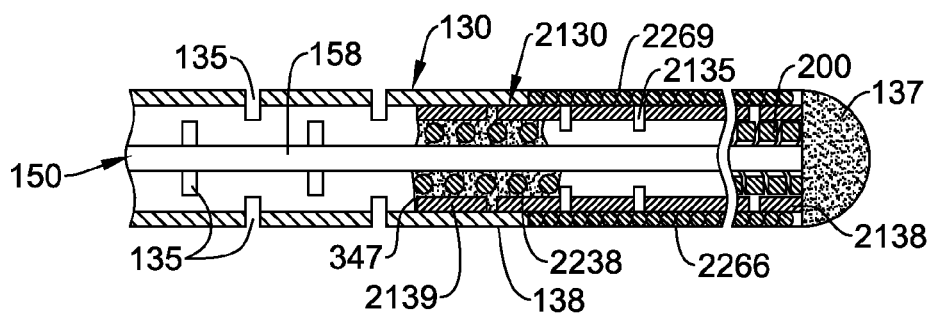
FIG. 22 is a cross-sectional side view illustrating the distal end of an embodiment of a medical device in accordance with the present invention having two tubular members and a coil on the outside.
Figure 24:
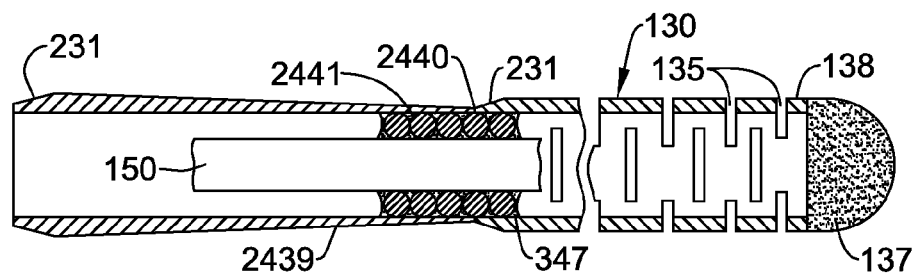
FIG. 24 is a cross-sectional side view illustrating the distal end of an embodiment of a medical device in accordance with the present invention a tapered portion of a tubular member in line with a slotted portion of a tubular member.

FIG. 20 illustrates an exemplary embodiment of the present invention having a tubular member 130 with unequally sized slots 1835a and 1835b of the configuration illustrated in FIG. 18. Other embodiments may have slots 135 as shown in FIG. 19, for another example, or may have equally sized slots 135 unequally spaced around the axis. Steerable medical device 2000 may include tubular member 130, core wire 150, control knob 2052, and tip 137. Tubular member 130 and core wire 150 may extend coaxially from control knob 2052 to distal tip 137. In this embodiment, tubular member 130 may consist of two or more tubes or tubular members attached with one or more joints, such as joint 140, or may consist of one tube, which may be slotted at least at distal end 138. For example, embodiments may be arranged similarly to what is shown in FIG. 7 (with the two tubular members 130 and 730 in line), similarly to what is shown in FIG. 21 (with the two tubular members 130 and 2130 arranged coaxially), similarly to what is shown in FIG. 22 (with the two tubular members arranged partially coaxially), or similarly to what is shown in FIG. 24 (with the two tubular members 130 and 2439 in line or being sections of the same tubular member). Core wire 150 may be stainless steel, nitinol, or a combination, as examples, and may have single or multiple strands.

Medical device 2000 may be steerable by controlling the shape or amount or angle of bend 133 by applying tension to core wire 150, for example, with control knob 2052. Increasing the angle of bend 133 may be accomplished, for example, by pulling on or turning (screwing) control knob 2052 relative to tubular member 130, inducing bending at unequally sized or offset slots 1835a and 1835b. Unequally sized slots 1835a and 1835b may be located along a portion of tubular member 130, for example, where bend 133 is desired. This location may be at or near distal end 138, for example. In one embodiment, medical device 2000 is a guidewire, and control knob 2052 is removable to guide a catheter over device 2000. In other embodiments, tubular member 130 may function as a catheter, which may be usable without a separate guidewire.

Further, in various embodiments of the present invention, it may be advantageous to reduce the compressive stiffness along the axis or column strength or stiffness of at least part of the medical device or tubular member 130, for example, to avoid dissection of vasculature 105. In the embodiment illustrated in FIG. 18, a compressive load on tubular member 130 may cause it to tend to bend in the direction of slots 1835a. In contrast, in the embodiment illustrated in FIG. 19, a compressive load on tubular member 130 may cause it to form a helical shape, bend in a direction determined by anatomy 101, or just shorten in length along its axis.

The present invention also includes various features for obtaining the desired torsional and bending stiffness of a medical device such as guidewire 100. Accordingly, FIG. 20 also illustrates a feature of many embodiments of the present invention, namely proximal hypotube or sleeve 2062. Sleeve 2062 may be shrunk fit in place or may be bonded to tubular member 130 (or to proximal section 159 of core wire 150, for example, in the embodiment illustrated in FIG. 1), for example with an adhesive, at least at the ends of sleeve 2062. Sleeve 2062 may be a second tubular member, and may increase the stiffness, strength, or both, of the part or parts it is bonded to (e.g., tubular member 130), in torsion, bending, tension, or a combination thereof. In some embodiments, sleeve 2062 may be made of a stiffer material than that to which it is bonded. For example, in the exemplary embodiment illustrated in FIG. 20, tubular member 130 may be nitinol, and sleeve 2062 may be stainless steel. In such embodiments, sleeve 2062 may cover only the proximal end of the medical device or tubular member 130. In some embodiments, sleeve 2062 may be at least partially slotted, or its outside diameter tapered, to reduce or control its bending stiffness. For example, sleeve 2062 may be slotted along its length or at its distal end similarly to tubular member 130. In some embodiments, control knob 2052 (or chuck 152) may attach or clamp to proximal sleeve 2062. In some embodiments, such as catheters, sleeve 2062 may substantially comprise a polymer material, and may seal slots 135.

FIG. 21 illustrates another exemplary embodiment of the present invention having tubular member 2130, which may share a common axis with tubular member 130. Tubular member 2130 may be concentric with tubular member 130 as shown. Tubular member 2130 may be inside tubular member 130, and tubular member 2130 may have a plurality of slots 2135 configured to make tubular member 2130 more flexible in bending. Tubular member 2130 may be slotted similarly to tubular member 130, and slots 2135 may be similar in arrangement, configuration, or both, to slots 135. Tubular member 2130 may have proximal end 2139 which may be at or near joint 140, and distal end 2138, which may be located proximal to distal end 138 of tubular member 130 as shown. A substantially radiopaque marker such as coil 200 may be located at distal end 2138 or distal to tubular member 2130. Tubular member 2130 may be made of materials identified herein for tubular member 130, and may be attached to coil wire 150, tubular member 130, or both, at proximal end 2139, distal end 2138, or both, for example, with solder or adhesive 347.

Still referring to FIG. 21, in some embodiments of the present invention, part or all of tubular member 130, tubular member 2130, or both, may lack slots 135 or 2135. For instance, one tubular member (130 or 2130) may lack slots (135 or 2135) over its entire length, while the other tubular member (130 or 2130) may contain slots (135 or 2135). In some such embodiments, part or all of tubular member 130, tubular member 2130, or both, may contain slots 135 or 2135 at one or both ends, for example, to smooth the transition in stiffness at that location. In some embodiments, portions of tubular member 130, tubular member 2130, or both, that lack slots 135 or 2135, may be tapered, for example by grinding, to reduce or control the bending stiffness in such locations.

As illustrated, some embodiments of the present invention having two tubular members (e.g., 130 and 2130) may have one or more abrupt changes in cross-sectional dimension or diameter of core wire 150, such as steps 2151, 2152, or both, which may be at the proximal ends of the tubular members. For example, tubular member 2130 may abut against step 2151, and tubular member 2130 may abut against step 2152.

Steps 2151 and 2152 may be located farther apart along the axis of core wire 150 than what is shown. Other embodiments may have a gradual taper in core wire 150 at joint 140, may comprise coils such as those illustrated in other figures, or may omit section 159 of core wire 150 proximal to proximal ends 139 and 2139. Some embodiments having two tubular members may be used in conjunction with extended coil tip 300 described above.

The embodiment of the present invention with concentric tubular members 130 and 2130 illustrated in FIG. 21 may have better resistance to kinking and better fatigue life than other alternatives, such as alternatives having a single tubular member 130 with fewer slots 135 or a greater wall thickness. Tubular members 130 and 2130 may be slotted separately or at the same time (e.g., in concentric configuration). In an exemplary embodiment, tubular member 130 may have an OD of 0.0135 inches and an ID of 0.0096 inches, and tubular member 2130 may have an OD of 0.0095 inches and an ID of 0.006 inches.

In some embodiments of the present invention, it may be desirable for all or part of the outside diameter of a medical device such as guidewire 100 to taper gradually or incrementally (e.g., by stepping) to a smaller OD at distal tip 137. This tapering may facilitate producing a lower bending stiffness in the distal direction. In addition, a smaller outside diameter in the distal end may be desirable, for example, where the medical device is to navigate through progressively smaller vasculature 105, and less space is available where distal end 138 is to navigate. As mentioned with reference to FIG. 1, tubular member 130 may have a smaller outside diameter than at least part of proximal section 159 of core wire 150. In some embodiments, for example, core wire 150 may taper gradually or incrementally from proximal end 154 to joint 140, for example, and may have a larger OD at end 154 than at joint 140. In another embodiment, proximal section 159 of core wire 150 may have a substantially constant OD, which may be larger than the OD of tubular member 130.

In the alternative, or in addition, the OD of tubular member 130 may taper in the distal direction. This taper may be a continuous gradual taper or an incremental taper, for example. The inside diameter (ID) of tubular member 130 may also reduce in the distal direction, or may remain constant. Thus, the wall thickness of tubular member 130 may also reduce gradually or incrementally in the distal direction along tubular member 130, or in some embodiments, may remain substantially constant.

Tubular member 130 may be tapered, for example, by machining or grinding its outside surface. In another embodiment, a plurality of different outside diameter sections of tubular member 130 may be joined together forming a tubular member 130 that tapers incrementally, for example, in one or more steps or tapered portions. The different outside diameter sections may butt together for joining or may overlap for a distance concentrically, for example, and may be joined with an adhesive or solder joint or a weld, for example. In such incrementally tapered embodiments of tubular member 130, the steps or changes in outside diameter may be machined or ground to form a chamfer or gradual taper, either along the entire length of tubular member 130 (i.e., a continuous taper) or between sections having substantially constant diameters (i.e., an incremental taper). Such chamfers or gradual tapers at changes in diameter may reduce friction and facilitate navigation of the medical device through anatomy 101. Chamfering or tapering these changes in diameter may also produce more gradual changes in stiffness, reduce stress concentration, or both.

As an exemplary embodiment, and as shown best in FIG. 22, distal end 2138 of smaller concentric tubular member 2130 may extend substantially distal to distal end 138 of larger tubular member 130. Distal tip 137 may be approximately the same size (e.g., diameter) as the OD of distal end 2138 of tubular member 2130, and may attach thereto, to distal section 158 of core wire 150, or both. In some embodiments, proximal end 2139 of tubular member 2130 may be where shown in FIG. 21, while in other embodiments, proximal end 2139 of tubular member 2130 may be just proximal to distal end 138 of tubular member 130 as shown in FIG. 22. For example, proximal end 2139 of tubular member 2130 may be far enough proximal to distal end 138 of tubular member 130 to allow space for a satisfactory joint between proximal end 2139 of tubular member 2130 and distal end 138 of tubular member 130. Such a joint may use solder or adhesive 347, for example. In some embodiments, a bushing or coil 2238 may be located between tubular member 130, tubular member 2130, or both, or between one or both tubular members (e.g., 130 and 2130) and distal section 158 of core wire 150. Tubular member 130, tubular member 2130, or both, may be attached to distal section 158 of core wire 150 at that location, for example with solder or adhesive 347 (or a combination of both), which may surround bushing or coil 2238.

Referring back to FIG. 21, also illustrated is a feature of many embodiments of the present invention, sleeve 2162. Sleeve 2162 may be similar to sleeve 2062 illustrated in FIG. 20 and described above. Sleeve 2162 may be substantially comprised of a flexible material such as a polymer, and may cover some or all of slots 135 in tubular member 130. Sleeve 2162 may cover all or part of proximal section 159 of core wire 150 as well, or instead. Further, in embodiments wherein tubular member 2130 extends distal to distal end 138 of tubular member 130, sleeve 2162 may extend distal to distal end 138 of tubular member 130. Thus, sleeve 2162 may cover at least part of tubular member 2130 and slots 2135 therein. In some such embodiments, sleeve 2162 may taper or be formed with a smaller OD distal to distal end 138 of tubular member 130.

Sleeve 2162 may be shrunk over tubular member 130, tubular member 2130, proximal section 159 of core wire 150, or a combination thereof, or may fit loosely (e.g., with a clearance fit) over other components, and may be affixed for example, with an adhesive. Sleeve 2162 may be affixed, for example, at both of its ends. In some embodiments, sleeve 2162 may be affixed at one or more intermediate locations as well. Sleeve 2162 may improve the lubricity of tubular member 130 by covering slots 135 and preventing friction between slots 135 and anatomy 101. Sleeve 2162 may also seal slots 135, for example, to facilitate using the medical device as a catheter. Further, Sleeve 2162 may increase the stiffness or strength of the medical device, may increase the OD of the medical device, or a combination of these effects. In comparison with other changes that may increase stiffness or OD, sleeve 2162 may avoid reducing the maximum radius of bend that can be achieved without plastic deformation, may avoid reducing fatigue life for a given radius of bend, or both.

In still another exemplary embodiment of the present invention illustrated by FIG. 21, tubular member 2130 may be a polymer tube. A polymer tubular member 2130 may not require slots 2135, but may increase stiffness without reducing maximum elastic bending radius or fatigue life of the medical device for a given radius of bend. Tubular member 2130 without slots 2135 may facilitate use of the medical device as a catheter, for example, in embodiments lacking core wire 150 or proximal section 159 thereof. In embodiments having at least distal section 158 of core wire 150, tubular member 2130 may also serve as a spacer between tubular member 130 and distal section 158 of core wire 150, and may keep section 158 of core wire 150 relatively centered within tubular member 130. Tubular member 2130 may prevent contact between tubular member 130 and core wire 150, reducing friction or wear. A polymer tubular member 2130 may be shrunk fit over distal section 158 of core wire 150, or may fit loosely thereover (e.g., with a clearance fit).

Figure 23:
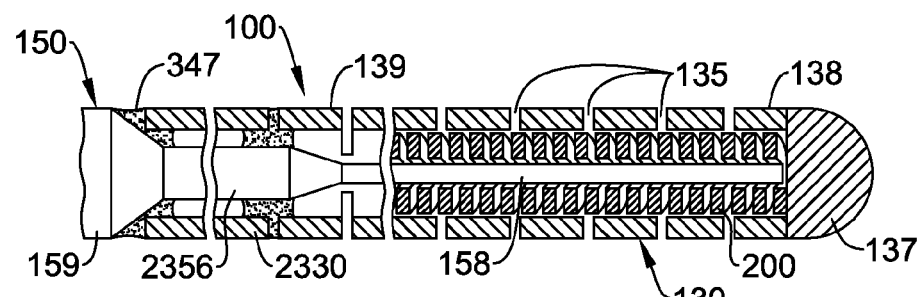
FIG. 23 is a cross-sectional side view illustrating the distal end of an embodiment of a medical device in accordance with the present invention having two tubular members arranged in line.

Another exemplary embodiment of the present invention having a second tubular member is illustrated in FIG. 23, which may be an alternate embodiment of guidewire 100. In this embodiment, second tubular member 2330 may be located in line with tubular member 130 and may be proximal to tubular member 130 as shown. Core wire 150 may extend through tubular member 2330 and at least part of tubular member 130, and may further extend proximal to tubular member 2330 as shown. Core wire 150 may have an intermediate section 2356 between proximal section 159 and distal section 158, and tubular member 2330 may be located at intermediate section 2356. The diameter of core wire 150 at section 2356 may be less than the diameter of core wire 150 at section 159, greater than the diameter of core wire 150 at section 158, or both. There may be an abrupt change in cross-sectional dimension or diameter (OD) of core wire 150 between proximal section 159 and intermediate section 2356 as shown, or there may be a gradual taper at that location. Similarly, there may be an abrupt change in cross-sectional dimension or diameter (OD) of core wire 150 between intermediate section 2356 and distal section 158, also as shown, or there may be a gradual taper at that location as well. Core wire 150 may have a great enough diameter at intermediate section 2356 to provide adequate strength and stiffness in torsion, as well as in bending.

As illustrated, such a guidewire 100 may also have a substantially radiopaque marker, such as coil 200, located at or near distal tip 137. Tubular member 2330 may be polymer, may be shrunk fit over section 2356 of core wire 150, or may be attached with an adhesive. Tubular member 2330 may be attached just at its ends, at intermediate locations as well, or along the entire length or at least a portion of tubular member 2330. The use of a polymer tubular member 2330, or tubular member 2330 made of a non-superelastic material, may reduce the necessary length of tubular member 130, reducing the cost of guidewire 100. Tubular member 2330 may also provide a more lubricious surface (e.g., in comparison with the surface of slotted tubular member 130), thus reducing friction between guidewire 100 and anatomy 101 at that location along the longitudinal axis. Further, tubular member 2330 may provide a larger diameter and stiffer section than section 2356 of core wire 150 alone, thus reducing the likelihood of dissection of vasculature 105 and increasing the stiffness of guidewire 100 at that location without reducing bending capability or fatigue resistance.

In other embodiments, tubular member 2330 may be slotted, and may be made of a superelastic metal. In some embodiments, tubular member 130 may be made of a substantially radiopaque material. In embodiments where tubular member 2330 is metal, it may be attached to other metal components with either solder or adhesive 337, for example.

FIG. 24 illustrates another exemplary embodiment of the present invention having a proximal portion of tubular member 130 or a second tubular member 2439 which may be attached to tubular member 130. Proximal portion of tubular member 130 or second tubular member 2439 may lack slots 135, but may be tapered at least at its OD in the distal direction as shown, providing a varying bending stiffness along at least part of its length. Thus, the wall thickness of proximal portion of tubular member 130 or second tubular member 2439 may become thinner in the distal direction, at least over part of proximal portion or second tubular member 2439. Tapering proximal portion of tubular member 130 or second tubular member 2439 may also serve to minimize or avoid a substantial change in stiffness at the proximal end of the section containing slots 135. This may serve to reduce fatigue at that location or at the most proximally located slot or slots 135.

In embodiments wherein distal portion of tubular member 130 or second tubular member 2439 is a separate piece from tubular member 130, there may be a joint 2440 between second tubular member 2439 and tubular member 130, an exemplary embodiment of which is shown. Bushing or coil 2441 may be located part way inside second tubular member 2439 and part way inside tubular member 130, and may be attached to each tubular member (i.e., 2439 and 130) with solder or adhesive 347. In embodiments having core wire 150, bushing or coil 2441 may also serve as a spacer centering core wire 150, and may be attached to core wire 150, for example, with solder or adhesive 347. In another exemplary embodiment of joint 2440, second tubular member 2439 may be welded to tubular member 130.

Distal portion of tubular member 130 or second tubular member 2439 may have an un-tapered (e.g., constant OD) section at its proximal end. In various embodiments, chamfers 231 may be provided at one or both ends of portion or member 2439. In embodiments wherein distal portion of tubular member 130 or second tubular member 2439 is part of tubular member 130, the assembly (i.e., tubular member 130) may be made of a superelastic material such as nitinol. In embodiments with a separate tubular member 2439, tubular member 130, tubular member 2439, or both may be made of a superelastic material such as nitinol. Or tubular member 2439 may be made of a polymer or stainless steel, for example. In some embodiments, tubular member 130 may be made of a substantially radiopaque material.

Referring once again to FIG. 22, also illustrated is another feature of various embodiments of the present invention, namely coil 2266. Coil 2266 may share a common axis with tubular member 130, tubular member 2130 (shown) or both. Further, coil 2266 may be concentric with and external to tubular member 130, tubular member 2130 (shown) or both. Coil 2266 may extend distally from tubular member 130 as shown. Thus, coil 2266 may form an extended coil tip 300 having a second tubular member 2130. Coil 2266 may be wound from wire having a substantially round cross section as shown, or may be an edge wound coil 200 as described above and shown in other figures. A lubricious coating 2269 may be applied over coil 2266, which may occupy all or part of the space between the windings of coil 2266. The same may be true for coil 345 illustrated in FIGS. 12-15, for example.

The rounded bumps of coil 2266 or 345 may provide a lower friction surface than the slotted exterior surface of tubular member 2130 or 130, for example. In addition, coating 2269 between the windings of coil 2266 may provide lubricity even when lubricious coating 2269 from the outermost surface has been worn away. Embodiments of the present invention having an extended coil tip 300, (illustrated in FIG. 3) may also have a coil 2266, a lubricious coating 2269, or both over coil 200. Coil 2266 may be particularly beneficial to lubricity in such embodiments wherein coil 200 has a cross section having sharp corners at its outside diameter. Coil 2266 may comprise a substantially radiopaque material, or a radiopaque material may be located inside coil 2266, for example, marker coil 200 shown inside tubular member 2130.

The above embodiments are illustrative of the present invention, but are not intended to limit its scope. Numerous modifications and alternative arrangements may be devised by those skilled in the art without departing from the spirit and scope of the present invention, and the appended claims are intended to cover such modifications and arrangements.

What is claimed is:

1. A medical device, comprising:
   a core member;
   a tubular member disposed over at least a portion of the core member and defining a space between the core member and the tubular member, the tubular member having a first group of slots and a second group of slots formed therein;
   wherein the tubular member has a longitudinal axis;
   wherein at least some of the slots in the first group of slots lie in a plane that is normal to the longitudinal axis of the tubular member;
   a filler material disposed within and filling the first group of slots, the filler material being disposed on an exterior surface of the core member, filling the space between the core member and the tubular member and extending radially from the exterior surface through the first group of slots; and
   wherein the second group of slots is free of the filler material.

2. The medical device of claim 1, further comprising an edge wound coil disposed adjacent to the core member.

3. The medical device of claim 1, wherein the filler material includes a polymer.

4. The medical device of claim 3, wherein the filler material includes polyurethane.

5. The medical device of claim 3, wherein the filler material includes epoxy.

6. The medical device of claim 1, wherein the first group of slots is disposed at a proximal end region of the tubular member.

7. A medical device, comprising:
   a core member;
   a tubular member disposed over at least a portion of the core member and defining a space between the core member and the tubular member, the tubular member having a plurality of slots formed therein, a proximal end region, and a distal end region;
   wherein at least a portion of the tubular member has a transverse cross-sectional shape that is circular;
   wherein the tubular member has a longitudinal axis and wherein at least some of the slots lie in a plane that is normal to the longitudinal axis of the tubular member;
   wherein at least some of the slots are disposed adjacent to the proximal end region of the tubular member and are filled with a filler material, the filler material being disposed on an exterior surface of the core member, filling the space between the core member and the tubular member, and extending radially from the exterior surface through the slots; and
   wherein at least some of the slots are disposed adjacent to the distal end region of the tubular member and are free of the filler material.

8. The medical device of claim 7, wherein the filler material includes a polymer.

9. The medical device of claim 8, wherein the filler material includes polyurethane.

10. The medical device of claim 8, wherein the filler material includes epoxy.

11. A medical device, comprising:
a core member;
a non-coiled tubular member coupled to the core member and defining a space between the core member and the non-coiled tubular member, the tubular member having a plurality of slots formed therein;
wherein the tubular member includes a proximal portion and a distal portion; and
means for increasing the stiffness of the proximal portion relative to the distal portion disposed within the slots in the proximal portion, wherein the means for increasing the stiffness of the proximal portion relative to the distal portion extends from the core member and fills the space between the core member and the non-coiled tubular member.

12. The medical device of claim 11, wherein the means for increasing the stiffness of the proximal portion relative to the distal portion includes a coating material disposed within and at least partially filling the slots in the proximal portion.

13. The medical device of claim 12, wherein the coating material includes a polymer.

14. The medical device of claim 12, wherein the coating material includes a polyurethane.

15. The medical device of claim 12, wherein the coating material includes an epoxy.

\* \* \* \* \*